United States Patent
Hofvander et al.

(10) Patent No.: US 6,784,338 B1
(45) Date of Patent: Aug. 31, 2004

(54) GENETICALLY ENGINEERED MODIFICATION OF POTATO TO FORM AMYLOPECTIN-TYPE STARCH

(75) Inventors: Per Hofvander, Falsterbo (SE); Per T. Persson, Kristianstad (SE); Anneli Tallberg, deceased, late of Lund (SE), by Maria Torper, Olof Torper, Tommy Tallberg, legal representatives; Olle Wikström, Kristianstad (SE)

(73) Assignee: BASF Plant Science GmbH, Ludwigshafen (DE)

(*) Notice: Subject to any disclaimer, the term of this patent is extended or adjusted under 35 U.S.C. 154(b) by 1826 days.

(21) Appl. No.: 08/070,455

(22) PCT Filed: Dec. 20, 1991

(86) PCT No.: PCT/SE91/00892

§ 371 (c)(1),
(2), (4) Date: Nov. 24, 1993

(87) PCT Pub. No.: WO92/11376

PCT Pub. Date: Jul. 9, 1992

(30) Foreign Application Priority Data

Dec. 21, 1990 (SE) .............................................. 9004096

(51) Int. Cl.[7] .................. C12N 15/82; C12N 15/29; A01H 5/00; A01H 5/10; C12P 19/04
(52) U.S. Cl. ................. 800/284; 800/278; 800/286; 800/287; 800/317.2; 435/101; 435/320.1; 435/417; 435/419; 536/23.6; 536/24.1; 536/24.5
(58) Field of Search ............................... 800/278, 284, 800/286, 287, 317.2, 205, 255, DIG. 42; 435/101, 320.1, 417, 419, 172.3, 240.4, 468; 536/23.6, 24.1, 24.5

(56) References Cited

U.S. PATENT DOCUMENTS 4,723,052 A * 2/1988 Cochran .................... 800/200
6,600,093 B1 * 7/2003 Visser et al. ............. 800/317.2

FOREIGN PATENT DOCUMENTS

| EP | 0 335 451 | 10/1989 |
| EP | 0 368 506 | 5/1990 |
| WO | WO 92/11376 | 7/1992 |

OTHER PUBLICATIONS

Stockhaus et al. EMBO Journal 9(9): 3013–3021 (1990).*
Sargeant et al. Starch 34(3): 89–92 (1982).*
Salomonsson et al. Starch 40(9): 325–328 (1994).*
Dubois et al. Analytical Chemistry 28(3): 350–356 (Mar. 1956).*
Smith, A. 1990. Planta 182:599–604.*
Dry et al. 1992. The Plant Journal 2(2): 193–202.*
Hovenkamp–Hermelink et al. 1987. Therm. Appl. Genet. 75: 217–221.*
van der Leij et al. 1991. Mol. Gen. Genet. 228 (1–2): 240–248.*
Visser et al. 1991 Mol. Gen. Genet. 225;289–296.*
Twell et al. 1987. Plant Mol. Biol. 9(4): 365–375.*
Visser, R. 1989. PhD Thesis, Rijksuniversiteit Groninger, pp. 1–141.*
"The Inhibition of the Expression of the Gene for Granule–Bound Starch Synthase in Potato by Antisense Constructs", R.G.F. Visser et al., Mol Gen Genet, vol. 225, pp. 289–296, (1991).
"Molecular Cloning and Partial Characterization of the Gene for Granule–Bound Starch Synthase from a Wildtype and an Amylose–Free Potato (*Solanum Turerosum L.*)", R.G.F. Visser et al., Plant Science, vol. 64, (1989), pp. 185–192.
"Structural and Functional Analysis of Two Waxy Gene Promoters from Potato", W. Rohde et al., J. Genet. & Breed., 44:311–315, (1990).
Hermansson, A. and Svegmark, K., Developments in the understanding of starch functionality, Trends in Food Science and Technology (reprinted in Elsevier Trends Journals), vol. 7, Nov. 1996, pp. 345–353.
Zobel, H., Ch. IX, Starch Gelatinization and Mechanical Properties, pp. 300–302.
Weisenborn, D., et al., Potato Starch Paste Behavior as Related to Some Physical/Chemical Properties, Journal of Food Science, vol. 59, No. 3, 1994, pp. 644–648.
Swinkels, J.J.M. et al., Compositions and Properties of Commercial Native Starches, Starch/Starke, vol. 37, No. 1. S., 1985, pp. 1–5.
Madsen, M.H. et al., Potato Starch During Growth, Starch/Starke, vol. 46, No. 7/8, 1996, pp. 245–249.
Larsson, C. et al.,Three isoforms of starch synthase and two isoforms of branching enzyme are present in potato tuber starch, Plant Science, vol. 117, 1996, pp. 9–16.
Kuipers, G.J. et al., Field evaluation of antisense RNA mediated inhibition of GBSS gene expression in potato, Euphytica, vol. 59, 1992, pp. 83–91.
Hergersberg, M., A Molecular Analysis of the Waxy Gene from *Solanum tuberosum* and expression of waxy antisense RNA in transgenic potatoes (*English translation of pp. 25–64 is attached*), 1988.

(List continued on next page.)

Primary Examiner—David T. Fox
(74) Attorney, Agent, or Firm—Morrison & Foerster LLP

(57) ABSTRACT

Genetically engineered modification of potato for suppressing the formation of amylose-type starch is described.

Three fragments for insertion in the antisense direction into the potato genome are also described. Moreover, antisense constructs, genes and vectors comprising said antisense fragments are described. Further a promoter for the gene coding for formation of granule-bound starch synthase and also the gene itself are described.

Also cells, plants, tubers, microtubers and seeds of potato comprising said antisense fragments are described.

Finally, amylopectin-type starch, both native and derivatised, derived from the potato that is modified in a genetically engineered manner, as well as a method of suppressing amylose formation in potato are described.

84 Claims, 6 Drawing Sheets

OTHER PUBLICATIONS

Kuipers, A.G.J. et al., Factors affecting the inhibition by antisense RNA of granule–bound starch synthase gene expression in potato, Mol Gen Genet, vol. 246, 1995, pp. 745–755.

Banks, W. and Greenwood, C.T., Starch and its Components, University Press, Edinburgh, pp. 77–79.

Bird, C.R. and Ray, J.A., Manipulation of Plant Gene Expression by Antisense RNA, Biotechnology and Genetic Engineering Reviews, Vo.. 9, 1991, Ch. 6, pp. 207–227.

Kuipers, A.G.J. et al., Field evaluation of transgenic potato plants expressing an antisense granule–bound starch synthase gene: increase of the antisense effect during tuber growth, Plant Molecular Biology, vol. 26, 1994, pp. 1759–1773.

Shannon, J.C. and Garwood, D.L., *Starch: Chemistry and Technology*, $2^{nd}$ Ed., (Edited by Whistler et al.), Chapter III: "Genetics and Physiology of Starch Development", 1984, pp. 32–33.

Hizukuri, S., Relationship Between the Distribution of the Chain Length of Amylopectin and the Crystalline Structure of Starch Granules, Carbohydrate Research, vol. 141, 1985, pp. 295–306.

Svegmark, K. et al., Molecular structures obtained from mixed amylose and potato starch dispersions and their rheological behaviour, Carbohydrate Polymers, vol. 22, 1993, pp. 19–29.

Murugesan, G., Characterisation of hot–water–soluble components of starches, Carbohydrate Research, vol. 242, 1993, pp. 203–215.

Hizukuri, S., Chapter 9: "Starch: Analytical Aspects", *Carbohydrates in Food*, MDI Decker, pp. 347, 392–393, 420–421.

Kuipers, A.G.J. et al., Formation and Deposition of Amylose in the Potato Tuber Starch Granule Are Affected by the Reduction of Granule–Bound Starch Synthase Gene Expression, The Plant Cell, vol. 6, 1994, pp. 43–52.

Roger, R. and Colonna, P., Evidence of the Presence of Large Aggregates Contaminating Amulose Solution, Carbohydrate Polymers, vol. 21, 1993, pp. 83–89.

Hizukuri, Polymodal Distribution of the Chain Lengths of Amylopectins, And Its Significance, Carbohydrate Research, vol.. 147, 1986, pp. 342–347.

Kalichevsky et al., The Retrogradation and Gelation of Amylopectins From Various Botanical Sources, Carbohydrate Research, vol. 498, 1990, pp. 49–55.

Radley, J.A., *Starch & Its Derivatives*, $4^{th}$ Ed., "Swelling and Gelation of Starch", 1968, p. 180–193.

Stryer, L., *Biochemistry*, $2^{nd}$ Ed., Chapter 26: "The Genetic Code", p. 629, [1975, 1981].

Sheehy, R.E. et al., Reduction of polygalacturonase activity in tomato fruit by antisense RNA, Proc. Natl. Acad. Sci. USA, vol. 85, 1988, pp. 8805–8809.

Visser, R.G.F. et al., Expression of a chimaeric granule–bound starch synthase–GUS gene in transgenic potato plants, Plant Molecular Biology, vol. 17, 1991, pp. 691–699.

Visser, R.G.F. et al., Efficient transformation of potato (*Solanum tuberosum* L.) using a binary vector in *Agrobacterium rhizogenes*, Theor Appl Genet (Theoretical and Applied Genetics), vol. 78, 1989, pp. 594–600.

Visser, R.G.F. et al., Expression and inheritance of inserted markers in binary vector carrying *Agrobacterium rhizogenes*–transformed potato (*Solanum tuberosum* L.), Theor Appl Genet, vol. 78, 1989, pp. 705–714.

Visser, R.G.F. et al. Transformation of homozygous diploid potato with an *Agrobacterium tumefaciens* binary vector system by adventitious shoot regeneration on leaf and stem segments, Plant Molecular Biology, vol. 12, 1989, pp. 329–337.

Visser, R.G.F. et al., Regeneration and transformation of potato by *Agrobacterium tumefaciens*, Plant Tissue Culture Manual B5: 1–9, 1991.

Schuch, W. et al., Control and manipultion of gene expression during tomato fruit ripening, Plant Molecular Biology, vol. 13, 1989, pp. 303–311.

Delauney, A.J. et al., A stable bifunctional antisense transcript inhibiting gene expression in transgenic plants, Proc. Natl. Acad. Sci. USA, vol. 85, 1988, pp. 4300–4304.

Smith, C.J.S. et al., Antisense RNA inhibition of polygalacturonase gene expression in transgenic tomatoes, Nature, vol. 334, 1988, pp. 724–726.

van der Krol, A.R. et al., An anti–sense chalcone synthase gene in transgenic plants inhibits flower pigmentation, Nature, vol. 333, 1988, pp. 866–869.

Wessler, M.S. and Fedoroff, N., Molecular Identification and Isolation of the Waxy Locus in Maize, Cell, vol. 35, 1983, pp. 225–233.

van der Leij, F.R., Visser, R.G.F. et al., Complementation of the amylose–free starch mutant of potato (*Solanum tuberosum.*) by the gene encoding granule–bound starch synthase, Theor Appl Genet, vol. 82, 1991, pp. 289–295.

Benfey, P.N. et al., The CaMN 35S enhancer contains at least two domains which can confer different developmental and tissue–specific expression patterns, The EMBO Journal, vol. 8, No. 8, 1989, pp. 2195–2202.

Rocha–Sosa, M. et al., Both development and metabolic signals activate the promoter of a class I patatin gene, The EMBO Journal, vol. 8, No. 1, 1989, pp. 23–29.

Schoch, T.J., Fractionation of Starch by Selective Precipitation with Butanol (Contribution from The Research Laboratory of Corn Products Refining Company), vol. 64, Dec. 1942, pp. 2957–2961.

Schoch, T.J., Adv. in Carb. Chem., vol. 1, The Fractionation of Starch, 1945, pp. 247–277.

Bates, F.L. et al., Amylose and Amylopectin Content of Starches Determined by their Iodine Complex Formation (Contribution form the Iowa Agricultural Experiment Station), vol. 65, pp. 142–148.

Feenstra, W.J. et al., Toward Potatoes Yielding Modified Starches, pp. 73–75, Poster Presentation, Sunday, Apr. 16, 1989, The European Workshop on Plant Biotechnology–Engineered Storage Products for the Agro Industry, Tanus Congress Centre, Parkhotel Und Karhaus Bad Soden a. Ts., Konsgsteiner Strabe 88, D–6232 Bod Soden a. Ts.

Accession No. X52580 Barley grp gene f . . . [gi: 18995], Submitted Apr. 4, 1990.

Accession No. X52417 *S. tuberosum* waxy . . . [gi:21615], Submitted Apr. 4, 1990.

Accession No. X52416 *S. tuberosum* waxy . . . [gi:21613], Submitted Apr. 4, 1990.

\* cited by examiner

FIG. 2 Result of restriction analysis. GBSS coding region including introns are marked in a darker tone.

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 342 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 217..342

(xi) SEQUENCE DESCRIPTION: SEQ ID NO:1:

```
TGCATGTTTC CCTACATTCT ATTTAGAATC GTGTTGTGGT GTATAAACGT TGTTTCATAT      60

CTCATCTCAT CTATTCTGAT TTTGATTCTC TTGCCTACTG TAATCGGTGA TAAATGTGAA     120

TGCTTCCTTT CTTCTCAGAA ATCAATTTCT GTTTTGTTTT TGTTCATCTG TAGCTTATTC     180

TCTGGTAGAT TCCCCTTTTT GTAGACCACA CATCAC ATG GCA AGC ATC ACA GCT      234
                                        Met Ala Ser Ile Thr Ala
                                          1               5

TCA CAC CAC TTT GTG TCA AGA AGC CAA ACT TCA CTA GAC ACC AAA TCA      282
Ser His His Phe Val Ser Arg Ser Gln Thr Ser Leu Asp Thr Lys Ser
         10              15                  20

ACC TTG TCA CAG ATA GGA CTC AGG AAC CAT ACT CTG ACT CAC AAT GGT      330
Thr Leu Ser Gln Ile Gly Leu Arg Asn His Thr Leu Thr His Asn Gly
        25              30                  35

TTA AGG GCT GTT                                                       342
Leu Arg Ala Val
    40
```

(2) INFORMATION FOR SEQ ID NO:2:

(i) SEQUENCE CHARACTERISTICS:
      (A) LENGTH: 2549 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
AACAAGCTTG ATGGGCTCCA ATCAACAACT AATACTAAGG TAACACCCAA GATGGCATCC      60

AGAACTGAGA CCAAGAGACC TGGATGCTCA GCTACCATTG TTTGTGGAAA GGGAATGAAC     120

TTGATCTTTG TGGGTACTGA GGTTGGTCCT TGGAGCAAAA CTGGTGGACT AGGTGATGTT     180

CTTGGTGGAC TACCACCAGC CCTTGCAGTA AGTCTTTCTT TCATTTGGTT ACCTACTCAT     240

TCATTACTTA TTTTGTTTAG TTAGTTTCTA CTGCATCAGT CTTTTTATCA TTTAGGCCCG     300
```

```
CGGACATCGG GTAATGACAA TATCCCCCCG TTATGACCAA TACAAAGATG CTTGGGATAC    360

TGGCGTTGCG GTTGAGGTAC ATCTTCCTAT ATTGATACGG TACAATATTG TTCTCTTACA    420

TTTCCTGATT CAAGAATGTG ATCATCTGCA GGTCAAAGTT GGAGACAGCA TTGAAATTGT    480

TCGTTTCTTT CACTGCTATA AACGTGGGGT TGATCGTGTT TTTGTTGACC ACCCAATGTT    540

CTTGGAGAAA GTAAGCATAT TATGATTATG AATCCGTCCT GAGGGATACG CAGAACAGGT    600

CATTTTGAGT ATCTTTTAAC TCTACTGGTG CTTTTACTCT TTTAAGGTTT GGGGCAAAAC    660

TGGTTCAAAA ATCTATGGCC CCAAAGCTGG ACTAGATTAT CTGGACAATG AACTTAGGTT    720

CAGCTTGTTG TGTCAAGTAA GTTAGTTACT CTTGATTTTT ATGTGGCATT TTACTCTTTT    780

GTCTTTAATC GTTTTTTTAA CCTTGTTTTC TCAGGCAGCC CTAGAGGCAC CTAAAGTTTT    840

GAATTTGAAC AGTAGCAACT ACTTCTCAGG ACCATATGGT AATTAACACA TCCTAGTTTC    900

AGAAAACTCC TTACTATATC ATTGTAGGTA ATCATCTTTA TTTTGCCTAT TCCTGCAGGA    960

GAGGATGTTC TCTTCATTGC CAATGATTGG CACACAGCTC TCATTCCTTG CTACTTGAAG   1020

TCAATGTACC AGTCCAGAGG AATCTACTTG AATGCCAAGG TAAAATTTCT TTGTATTCAC   1080

TCGATTGCAC GTTACCCTGC AAATCAGTAA GGTTGTATTA ATATATGATA AATTTCACAT   1140

TGCCTCCAGG TTGCTTTCTG CATCCATAAC ATTGCCTACC AAGGTCGATT TTCTTTCTCT   1200

GACTTCCCTC TTCTCAATCT TCCTGATGAA TTCAGGGGTT CTTTTGATTT CATTGATGGG   1260

TATGTATTTA TGCTTGAAAT CAGACCTCCA ACTTTTGAAG CTCTTTTGAT GCTAGTAAAT   1320

TGAGTTTTTA AAATTTTGCA GATATGAGAA GCCTGTTAAG GGTAGGAAAA TCAACTGGAT   1380

GAAGGCTGGG ATATTAGAAT CACATAGGGT GGTTACAGTG AGCCCATACT ATGCCCAAGA   1440

ACTTGTCTCT GCTGTTGACA AGGGAGTTGA ATTGGACAGT GTCCTTCGTA AGACTTGCAT   1500

AACTGGGATT GTGAATGGCA TGGATACACA AGAGTGGAAC CCAGCGACTG ACAAATACAC   1560

AGATGTCAAA TACGATATAA CCACTGTAAG ATAAGATTTT TCCGACTCCA GTATATACTA   1620

AATTATTTTG TATGTTTATG AAATTAAAGA GTTCTTGCTA ATCAAAATCT CTATACAGGT   1680

CATGGACGCA AAACCTTTAC TAAAGGAGGC TCTTCAAGCA GCAGTTGGCT TGCCTGTTGA   1740

CAAGAAGATC CCTTTGATTG GCTTCATCGG CAGACTTGAG GAGCAGAAAG GTTCAGATAT   1800

TCTTGTTGCT GCAATTCACA AGTTCATCGG ATTGGATGTT CAAATTGTAG TCCTTGTAAG   1860

TACCAAATGG ACTCATGGTA TCTCTCTTGT TGAGTTTACT TGTGCCGAAA CTGAAATTGA   1920

CCTGCTACTC ATCCTATGCA TCAGGGAACT GGCAAAAAGG AGTTTGAGCA GGAGATTGAA   1980

CAGCTCGAAG TGTTGTACCC TAACAAAGCT AAAGGAGTGG CAAAATTCAA TGTCCCTTTG   2040

GCTCACATGA TCACTGCTGG TGCTGATTTT ATGTTGGTTC CAAGCAGATT TGAACCTTGT   2100

GGTCTCATTC AGTTACATGC TATGCGATAT GGAACAGTAA GAACCAGAAG AGCTTGTACC   2160

TTTTTACTGA GTTTTTAAAA AAAGAATCAT AAGACCTTGT TTTCCATCTA AGTTTAATA    2220

ACCAACTAAA TGTTACTGCA GCAAGCTTTT CATTTCTGAA AATTGGTTAT CTGATTTTAA   2280

CGTAATCACA TGTGAGTCAG GTACCAATCT GTGCATCGAC TGGTGGACTT GTTGACACTG   2340

TGAAAGAAGG CTATACTGGA TTCCATATGG GAGCCTTCAA TGTTGAAGTA TGTGATTTTA   2400

CATCAATTGT GTACTTGTAC ATGGTCCATT CTCGTCTTGA TATACCCCTT GTTGCATAAA   2460

CATTAACTTA TTGCTTCTTG AATTTGGTTA GTGCGATGTT GTTGACCCAG CTGATGTGCT   2520

TAAGATAGTA ACAACAGTTG CTAGAGCTC                                    2549

(2) INFORMATION FOR SEQ ID NO:3:
```

(i) SEQUENCE CHARACTERISTICS:
    (A) LENGTH: 492 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: CDS
    (B) LOCATION: 1..15

(ix) FEATURE:
    (A) NAME/KEY: CDS
    (B) LOCATION: 101..218

(xi) SEQUENCE DESCRIPTION: SEQ ID NO:3:

```
GAG CTC TCC TGG AAG GTAAGTGTGA ATTTGATAAT TTGCGTAGGT ACTTCAGTTT         55
Glu Leu Ser Trp Lys
 1               5

GTTGTTCTCG TCAGCACTGA TGGATTCCAA CTGGTGTTCT TGCAG GAA CCT GCC          109
                                                  Glu Pro Ala
                                                    1

AAG AAA TGG GAG ACA TTG CTA TTG GGC TTA GGA GCT TCT GGC AGT GAA        157
Lys Lys Trp Glu Thr Leu Leu Leu Gly Leu Gly Ala Ser Gly Ser Glu
  5              10                  15

CCC GGT GTT GAA GGG GAA GAA ATC GCT CCA CTT GCC AAG GAA AAT GTA        205
Pro Gly Val Glu Gly Glu Glu Ile Ala Pro Leu Ala Lys Glu Asn Val
 20              25                  30                  35

GCC ACT CCT TAAATGAGCT TTGGTTATCC TTGTTTCAAC AATAAGATCA                254
Ala Thr Pro *

TTAAGCAAAC GTATTTACTA GCGAACTATG TAGAACCCTA TTATGGGGTC TCAATCATCT      314

ACAAAATGAT TGGTTTTTGC TGGGGAGCAG CAGCATATAA GGCTGTAAAA TCCTGGTTAA      374

TGTTTTTGTA GGTAAGGGCT ATTTAAGGTG GTGTGGATCA AAGTCAATAG AAAATAGTTA     434

TTACTAACGT TTGCAACTAA ATACTTAGTA ATGTAGCATA AATAATACTA GAACTAGT       492
```

(2) INFORMATION FOR SEQ ID NO:4:

(i) SEQUENCE CHARACTERISTICS:
        (A) LENGTH: 987 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
AAGCTTTAAC GAGATAGAAA ATTATGTTAC TCCGTTTTGT TCATTACTTA ACAAATGCAA       60

CAGTATCTTG TACCAAATCC TTTCTCTCTT TTCAAACTTT TCTATTTGGC TGTTGACGGA      120

GTAATCAGGA TACAAACCAC AAGTATTTAA TTGACTCCTC CGCCAGATAT TATGATTTAT      180

GAATCCTCGA AAAGCCTATC CATTAAGTCC TCATCTATGG ATATACTTGA CAGTATCTTC      240

CTGTTTGGGT ATTTTTTTTT CCTGCCAAGT GGAACGGAGA CATGTTATGA TGTATACGGG      300

AAGCTCGTTA AAAAAAAATA CAATAGGAAG AAATGTAACA ACATTGAAT GTTGTTTTA       360

ACCATCCTTC CTTTAGCAGT GTATCAATTT TGTAATAGAA CCATGCATCT CAATCTTAAT      420

ACTAAAATGC AACTTAATAT AGGCTAAACC AAGATAAGT AATGTATTCA ACCTTTAGAA      480

TTGTGCATTC ATAATTAGAT CTTGTTTGTC GTAAAAAATT AGAAATATA TTTACAGTAA      540

TTTGGAATAC AAAGCTAAGG GGGAAGTAAC TAATATTCTA GTGGAGGGAG GGACCAGTAC      600

CAGTACCTAG ATATTATTTT TAATTACTAT AATAATAATT TAATTAACAC GAGACATAGG      660
```

```
AATGTCAAGT GGTAGCGTAG GAGGGAGTTG GTTTAGTTTT TTAGATACTA GGAGACAGAA      720

CCGGACGGCC CATTGCAAGG CCAAGTTGAA GTCCAGCCGT GAATCAACAA AGAGAGGGCC      780

CATAATACTG TCGATGAGCA TTTCCCTATA ATACAGTGTC CACAGTTGCC TTCTGCTAAG      840

GGATAGCCAC CCGCTATTCT CTTGACACGT GTCACTGAAA CCTGCTACAA ATAAGGCAGG      900

CACCTCCTCA TTCTCACTCA CTCACTCACA CAGCTCAACA AGTGGTAACT TTTACTCATC      960

TCCTCCAATT ATTTCTGATT TCATGCA                                         987

(2) INFORMATION FOR SEQ ID NO:5:

(i) SEQUENCE CHARACTERISTICS:
         (A) LENGTH: 4964 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:5:

AAGCTTTAAC GAGATAGAAA ATTATGTTAC TCCGTTTTGT TCATTACTTA ACAAATGCAA       60

CAGTATCTTG TACCAAATCC TTTCTCTCTT TTCAAACTTT TCTATTTGGC TGTTGACGGA      120

GTAATCAGGA TACAAACCAC AAGTATTTAA TTGACTCCTC CGCCAGATAT TATGATTTAT      180

GAATCCTCGA AAAGCCTATC CATTAAGTCC TCATCTATGG ATATACTTGA CAGTATCTTC      240

CTGTTTGGGT ATTTTTTTTT CCTGCCAAGT GGAACGGAGA CATGTTATGA TGTATACGGG      300

AAGCTCGTTA AAAAAAAATA CAATAGGAAG AAATGTAACA AACATTGAAT GTTGTTTTTA      360

ACCATCCTTC CTTTAGCAGT GTATCAATTT TGTAATAGAA CCATGCATCT CAATCTTAAT      420

ACTAAAATGC AACTTAATAT AGGCTAAACC AAGATAAAGT AATGTATTCA ACCTTTAGAA      480

TTGTGCATTC ATAATTAGAT CTTGTTTGTC GTAAAAAATT AGAAAATATA TTTACAGTAA      540

TTTGGAATAC AAAGCTAAGG GGGAAGTAAC TAATATTCTA GTGGAGGGAG GGACCAGTAC      600

CAGTACCTAG ATATTATTTT TAATTACTAT AATAATAATT TAATTAACAC GAGACATAGG      660

AATGTCAAGT GGTAGCGTAG GAGGGAGTTG GTTTAGTTTT TTAGATACTA GGAGACAGAA      720

CCGGACGGCC CATTGCAAGG CCAAGTTGAA GTCCAGCCGT GAATCAACAA AGAGAGGGCC      780

CATAATACTG TCGATGAGCA TTTCCCTATA ATACAGTGTC CACAGTTGCC TTCTGCTAAG      840

GGATAGCCAC CCGCTATTCT CTTGACACGT GTCACTGAAA CCTGCTACAA ATAAGGCAGG      900

CACCTCCTCA TTCTCACTCA CTCACTCACA CAGCTCAACA AGTGGTAACT TTTACTCATC      960

TCCTCCAATT ATTTCTGATT TCATGCATGT TTCCCTACAT TCTATTATGA ATCGTGTTGT     1020

GGTGTATAAA CGTTGTTTCA TATCTCATCT CATCTATTCT GATTTTGATT CTCTTGCCTA     1080

CTGTAATCGG TGATAAATGT GAATGCTTCC TTTCTTCTCA GAAATCAATT TCTGTTTTGT     1140

TTTTGTTCAT CTGTAGCTTA TTCTCTGGTA GATTCCCCTT TTTGTAGACC ACACATCACA     1200

TGGCAAGCAT CACAGCTTCA CACCACTTTG TGTCAAGAAG CCAAACTTCA CTAGACACCA     1260

AATCAACCTT GTCACAGATA GGACTCAGGA ACCATACTCT GACTCACAAT GGTTTAAGGG     1320

CTGTTAACAA GCTTGATGGG CTCCAATCAA CAACTAATAC TAAGGTAACA CCCAAGATGG     1380

CATCCAGAAC TGAGACCAAG AGACCTGGAT GCTCAGCTAC CATTGTTTGT GGAAAGGGAA     1440

TGAACTTGAT CTTTGTGGGT ACTGAGGTTG GTCCTTGGAG CAAAACTGGT GGACTAGGTG     1500

ATGTTCTTGG TGGACTACCA CCAGCCCTTG CAGTAAGTCT TTCTTTCATT TGGTTACCTA     1560

CTCATTCATT ACTTATTTTG TTTAGTTAGT TTCTACTGCA TCAGTCTTTT TATCATTTAG     1620
```

-continued

```
GCCCGCGGAC AGCGGGTAAT GACAATATCC CCCCGTTATG ACCAATACAA AGATGCTTGG      1680

GATACTGGCG TTGCGGTTGA GGTACATCTT CCTATATTGA TACGGTACAA TATTGTTCTC      1740

TTACATTTCC TGATTCAAGA ATGTGATCAT CTGCAGGTCA AAGTTGGAGA CAGCATTGAA      1800

ATTGTTCGTT TCTTTCACTG CTATAAACGT GGGGTTGATC GTGTTTTTGT TGACCACCCA      1860

ATGTTCTTGG AGAAAGTAAG CATATTATGA TTATGAATCC GTCCTGAGGG ATACGCAGAA      1920

CAGGTCATTT TGAGTATCTT TTAACTCTAC TGGTGCTTTT ACTCTTTTAA GGTTTGGGGC      1980

AAAACTGGTT CAAAAATCTA TGGCCCCAAA GCTGGACTAG ATTATCTGGA CAATGAACTT      2040

AGGTTCAGCT TGTTGTGTCA AGTAAGTTAG TTACTCTTGA TTTTTATGTG GCATTTTACT      2100

CTTTTGTCTT TAATCGTTTT TTTAACCTTG TTTTCTCAGG CAGCCCTAGA GGCACCTAAA      2160

GTTTTGAATT TGAACAGTAG CAACTACTTC TCAGGACCAT ATGGTAATTA ACACATCCTA      2220

GTTTCAGAAA ACTCCTTACT ATATCATTGT AGGTAATCAT CTTTATTTTG CCTATTCCTG      2280

CAGGAGAGGA TGTTCTCTTC ATTGCCAATG ATTGGCACAC AGCTCTCATT CCTTGCTACT      2340

TGAAGTCAAT GTACCAGTCC AGAGGAATCT ACTTGAATGC CAAGGTAAAA TTTCTTTGTA      2400

TTCACTCGAT TGCACGTTAC CCTGCAAATC AGTAAGGTTG TATTAATATA TGATAAATTT      2460

CACATTGCCT CCAGGTTGCT TTCTGCATCC ATAACATTGC CTACCAAGGT CGATTTTCTT      2520

TCTCTGACTT CCCTCTTCTC AATCTTCCTG ATGAATTCAG GGGTTCTTTT GATTTCATTG      2580

ATGGGTATGT ATTTATGCTT GAAATCAGAC CTCCAACTTT TGAAGCTCTT TTGATGCTAG      2640

TAAATTGAGT TTTTAAAATT TTGCAGATAT GAGAAGCCTG TTAAGGGTAG GAAAATCAAC      2700

TGGATGAAGG CTGGGATATT AGAATCACAT AGGGTGGTTA CAGTGAGCCC ATACTATGCC      2760

CAAGAACTTG TCTCTGCTGT TGACAAGGGA GTTGAATTGG ACAGTGTCCT TCGTAAGACT      2820

TGCATAACTG GGATTGTGAA TGGCATGGAT ACACAAGAGT GGAACCCAGC GACTGACAAA      2880

TACACAGATG TCAAATACGA TATAACCACT GTAAGATAAG ATTTTTCCGA CTCCAGTATA      2940

TACTAAATTA TTTTGTATGT TTATGAAATT AAAGAGTTCT TGCTAATCAA AATCTCTATA      3000

CAGGTCATGG ACGCAAAACC TTTACTAAAG GAGGCTCTTC AAGCAGCAGT TGGCTTGCCT      3060

GTTGACAAGA AGATCCCTTT GATTGGCTTC ATCGGCAGAC TTGAGGAGCA GAAAGGTTCA      3120

GATATTCTTG TTGCTGCAAT TCACAAGTTC ATCGGATTGG ATGTTCAAAT TGTAGTCCTT      3180

GTAAGTACCA AATGGACTCA TGGTATCTCT CTTGTTGAGT TTACTTGTGC CGAAACTGAA      3240

ATTGACCTGC TACTCATCCT ATGCATCAGG GAACTGGCAA AAAGGATTTT GAGCAGGAGA      3300

TTGAACAGCT CGAAGTGTTG TACCCTAACA AAGCTAAAGG AGTGGCAAAA TTCAATGTCC      3360

CTTTGGCTCA CATGATCACT GCTGGTGCTG ATTTTATGTT GGTTCCAAGC AGATTTGAAC      3420

CTTGTGGTCT CATTCAGTTA CATGCTATGC GATATGGAAC AGTAAGAACC AGAAGAGCTT      3480

GTACCTTTTT ACTGAGTTTT TAAAAAAAGA ATCATAAGAC CTTGTTTTCC ATCTAAAGTT      3540

TAATAACCAA CTAAATGTTA CTGCAGCAAG CTTTTCATTT CTGAAAATTG GTTATCTGAT      3600

TTTAACGTAA TCACATGTGA GTCAGGTACC AATCTGTGCA TCGACTGGTG GACTTGTTGA      3660

CACTGTGAAA GAAGGCTATA CTGGATTCCA TATGGGAGCC TTCAATGTTG AAGTATGTGA      3720

TTTTACATCA ATTGTGTACT TGTACATGGT CCATTCTCGT CTTGATATAC CCCTTGTTGC      3780

ATAAACATTA ACTTATTGCT TCTTGAATTT GGTTAGTGCG ATGTTGTTGA CCCAGCTGAT      3840

GTGCTTAAGA TAGTAACAAC AGTTGCTAGA GCTCTTGCAG TCTATGGCAC CCTCGCATTT      3900

GCTGAGATGA TAAAAAATTG CATGTCAGAG GAGCTCTCCT GGAAGGTAAG TGTGAATTTG      3960
```

```
ATAATTTGCG TAGGTACTTC AGTTTGTTGT TCTCGTCAGC ACTGATGGAT TCCAACTGGT      4020

GTTCTTGCAG GAACCTGCCA AGAAATGGGA GACATTGCTA TTGGGCTTAG GAGCTTCTGG      4080

CAGTGAACCC GGTGTTGAAG GGGAAGAAAT CGCTCCACTT GCCAAGGAAA ATGTAGCCAC      4140

TCCTTAAATG AGCTTTGGTT ATCCTTGTTT CAACAATAAG ATCATTAAGC AAACGTATTT      4200

ACTAGCGAAC TATGTAGAAC CCTATTATGG GGTCTCAATC ATCTACAAAA TGATTGGTTT      4260

TTGCTGGGGA GCAGCAGCAT ATAAGGCTGT AAAATCCTGG TTAATGTTTT TGTAGGTAAG      4320

GGCTATTTAA GGTGGTGTGG ATCAAAGTCA ATAGAAAATA GTTATTACTA ACGTTTGCAA      4380

CTAAATACTT AGTAATGTAG CATAAATAAT ACTAGAACTA GTAGCTAATA TATATGCGTG      4440

AATTTGTTGT ACCTTTTCTT GCATAATTAT TTGCAGTACA TATATAATGA AAATTACCCA      4500

AGGAATCAAT GTTTCTTGCT CCGTCCTCCT TTGATGATTT TTTACGCAAT ACAGAGCTAG      4560

TGTGTTATGT TATAAATTTT GTTTAAAAGA AGTAATCAAA TTCAAATTAG TTGTTTGGTC      4620

ATATGAAAGA AGCTGCCAGG CTAACTTTGA GGAGATGGCT ATTGAATTTC AAAATGATTA      4680

TGTGAAAACA ATGCAACATC TATGTCAATC AACACTTAAA TTATTGCATT TAGAAAGATA      4740

TTTTTGAGCC CATGACACAT TCATTCATAA AGTAAGGTAG TATGTATGAT TGAATGGACT      4800

ACAGCTCAAT CAAAGCATCT CCTTTACATA ACGGCACTGT CTCTTGTCTA CTACTCTATT      4860

GGTAGTAGTA GTAGTAATTT TACAATCCAA ATTGAATAGT AATAAGATGC TCTCTATTTA      4920

CTAAAGTAGT AGTATTATTC TTTCGTTACT CTAAAGCAAC AAAA                      4964
```

(2) INFORMATION FOR SEQ ID NO:6:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1..69
        (D) OTHER INFORMATION: /note= "Amino acid sequence encoded
            by nucleotides 1-207 of SEQ ID NO. 2."

(xi) SEQUENCE DESCRIPTION: SEQ ID NO:6:

```
Asn Lys Leu Asp Gly Leu Gln Ser Thr Thr Asn Thr Lys Val Thr Pro
1               5                   10                  15

Lys Met Ala Ser Arg Thr Glu Thr Lys Arg Pro Gly Cys Ser Ala Thr
            20                  25                  30

Ile Val Cys Gly Lys Gly Met Asn Leu Ile Phe Val Gly Thr Glu Val
        35                  40                  45

Gly Pro Trp Ser Lys Thr Gly Gly Leu Gly Asp Val Leu Gly Gly Leu
    50                  55                  60

Pro Pro Ala Leu Ala
65
```

(2) INFORMATION FOR SEQ ID NO:7:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide

```
    (ix) FEATURE:
         (A) NAME/KEY: Modified-site
         (B) LOCATION: 1..27
         (D) OTHER INFORMATION: /note= "Amino acid sequence encoded
             by nucleotides 296-377 of SEQ ID NO. 2."

(xi) SEQUENCE DESCRIPTION: SEQ ID NO:7:

Ala Arg Gly His Arg Val Met Thr Ile Ser Pro Arg Tyr Asp Gln Tyr
1               5                  10                  15

Lys Asp Ala Trp Asp Thr Gly Val Ala Val Glu
            20                  25

(2) INFORMATION FOR SEQ ID NO:8:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 1..33
         (D) OTHER INFORMATION: /note= "Amino acid sequence encoded
             by nucleotides 452-550 of SEQ ID NO. 2."

(xi) SEQUENCE DESCRIPTION: SEQ ID NO:8:

Val Lys Val Gly Asp Ser Ile Glu Ile Val Arg Phe Phe His Cys Tyr
1               5                  10                  15

Lys Arg Gly Val Asp Arg Val Phe Val Asp His Pro Met Phe Leu Glu
            20                  25                  30

Lys (2) INFORMATION FOR SEQ ID NO:9:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 1..30
         (D) OTHER INFORMATION: /note= "Amino acid sequence encoded
             by nucleotides 647-736 of SEQ ID NO. 2."

(xi) SEQUENCE DESCRIPTION: SEQ ID NO:9:

Val Trp Gly Lys Thr Gly Ser Lys Ile Tyr Gly Pro Lys Ala Gly Leu
1               5                  10                  15

Asp Tyr Leu Asp Asn Glu Leu Arg Phe Ser Leu Leu Cys Gln
            20                  25                  30

(2) INFORMATION FOR SEQ ID NO:10:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
```

```
            (B) LOCATION: 1..21
            (D) OTHER INFORMATION: /note= "Amino acid sequence encoded
                by nucleotides 815-878 of SEQ ID NO. 2."

(xi) SEQUENCE DESCRIPTION: SEQ ID NO:10:

Ala Ala Leu Glu Ala Pro Lys Val Leu Asn Leu Asn Ser Ser Asn Tyr
1               5                  10                  15

Phe Ser Gly Pro Tyr
            20

(2) INFORMATION FOR SEQ ID NO:11:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1..34
        (D) OTHER INFORMATION: /note= "Amino acid sequence encoded
                by nucleotides 878 and 959-1059 of SEQ ID NO. 2."

(xi) SEQUENCE DESCRIPTION: SEQ ID NO:11:

Gly Glu Asp Val Leu Phe Ile Ala Asn Asp Trp His Thr Ala Leu Ile
1               5                  10                  15

Pro Cys Tyr Leu Lys Ser Met Tyr Gln Ser Arg Gly Ile Tyr Leu Asn
            20                  25                  30

Ala Lys (2) INFORMATION FOR SEQ ID NO:12:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1..38
        (D) OTHER INFORMATION: /note= "Amino acid sequence encoded
                by nucleotides 1150-1263 of SEQ ID NO 2."

(xi) SEQUENCE DESCRIPTION: SEQ ID NO:12:

Val Ala Phe Cys Ile His Asn Ile Ala Tyr Gln Gly Arg Phe Ser Phe
1               5                  10                  15

Ser Asp Phe Pro Leu Leu Asn Leu Pro Asp Glu Phe Arg Gly Ser Phe
            20                  25                  30

Asp Phe Ile Asp Gly Tyr
            35

(2) INFORMATION FOR SEQ ID NO:13:

(i) SEQUENCE CHARACTERISTICS:
        (A) LENGTH: 79 amino acids
        (B) TYPE: amino acid
        (C) STRANDEDNESS: single
        (D) TOPOLOGY: linear (ii) MOLECULE TYPE: peptide (ix) FEATURE:
```

(A) NAME/KEY: Modified-site
(B) LOCATION: 1..79
(D) OTHER INFORMATION: /note= "Amino acid sequence encoded
    by nucleotides 1349-1585 of SEQ ID NO 2."

(xi) SEQUENCE DESCRIPTION: SEQ ID NO:13:

Lys Pro Val Lys Gly Arg Lys Ile Asn Trp Met Lys Ala Gly Ile Leu
1               5                   10                  15

Glu Ser His Arg Val Val Thr Val Ser Pro Tyr Tyr Ala Gln Glu Leu
                20                  25                  30

Val Ser Ala Val Asp Lys Gly Val Glu Leu Asp Ser Val Leu Arg Lys
            35                  40                  45

Thr Cys Ile Thr Gly Ile Val Asn Gly Met Asp Thr Gln Glu Trp Asn
        50                  55                  60

Pro Ala Thr Asp Lys Tyr Thr Asp Val Lys Tyr Asp Ile Thr Thr
65                  70                  75

(2) INFORMATION FOR SEQ ID NO:14:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1..59
        (D) OTHER INFORMATION: /note= "Amino acid sequence encoded
            by nucleotides 1676-1855 of SEQ ID NO 2."

(xi) SEQUENCE DESCRIPTION: SEQ ID NO:14:

Val Met Asp Ala Lys Pro Leu Leu Lys Glu Ala Leu Gln Ala Ala Val
1               5                   10                  15

Gly Leu Pro Val Asp Lys Lys Ile Pro Leu Ile Gly Phe Ile Gly Arg
                20                  25                  30

Leu Glu Glu Gln Lys Gly Ser Asp Ile Leu Ala Val Ala Ile His Lys
            35                  40                  45

Phe Ile Gly Leu Asp Val Gln Ile Val Val Leu
        50                  55

(2) INFORMATION FOR SEQ ID NO:15:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1..64
        (D) OTHER INFORMATION: /note= "Amino acid sequence encoded
            by nucleotides 1945-2136 of SEQ ID NO 2."

(xi) SEQUENCE DESCRIPTION: SEQ ID NO:15:

Gly Thr Gly Lys Lys Glu Phe Glu Gln Glu Ile Glu Gln Leu Glu Val
1               5                   10                  15

Leu Tyr Pro Asn Lys Ala Lys Gly Val Ala Lys Phe Asn Val Pro Leu
                20                  25                  30

Ala His Met Ile Thr Ala Gly Ala Asp Phe Met Leu Val Pro Ser Arg

```
              35                  40                  45
Phe Glu Pro Cys Gly Leu Ile Gln Leu His Ala Met Arg Tyr Gly Thr
 50                  55                  60
```

(2) INFORMATION FOR SEQ ID NO:16:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1..29
        (D) OTHER INFORMATION: /note= "Amino acid sequence encoded
            by nucleotides 2301-2386 of SEQ ID NO 2."

(xi) SEQUENCE DESCRIPTION: SEQ ID NO:16:

```
Val Pro Ile Cys Ala Ser Thr Gly Gly Leu Val Asp Thr Val Lys Glu
 1               5                  10                  15

Gly Tyr Thr Gly Phe His Met Gly Ala Phe Asn Val Glu
                 20                  25
```

(2) INFORMATION FOR SEQ ID NO:17:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1..19
        (D) OTHER INFORMATION: /note= "Amino acid sequence encoded
            by nucleotides 2492-2459 of SEQ ID NO 2."

(xi) SEQUENCE DESCRIPTION: SEQ ID NO:17:

```
Cys Asp Val Val Asp Pro Ala Asp Val Leu Lys Ile Val Thr Thr Val
 1               5                  10                  15

Ala Arg Ala
```

(2) INFORMATION FOR SEQ ID NO:18:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1..111
        (D) OTHER INFORMATION: /note= "Amino acid sequence encoded
            by nucleotides 1200-1532 of SEQ ID NO 5."

(xi) SEQUENCE DESCRIPTION: SEQ ID NO:18:

```
Met Ala Ser Ile Thr Ala Ser His His Phe Val Ser Arg Ser Gln Thr
 1               5                  10                  15

Ser Leu Asp Thr Lys Ser Thr Leu Ser Gln Ile Gly Leu Arg Asn His
                 20                  25                  30
```

-continued

```
Thr Leu Thr His Asn Gly Leu Arg Ala Val Asn Lys Leu Asp Gly Leu
        35                  40                  45

Gln Ser Thr Thr Asn Thr Lys Val Thr Pro Lys Met Ala Ser Arg Thr
50                  55                  60

Glu Thr Lys Arg Pro Gly Cys Ser Ala Thr Ile Val Cys Gly Lys Gly
65                  70                  75                  80

Met Asn Leu Ile Phe Val Gly Thr Glu Val Gly Pro Trp Ser Lys Thr
                85                  90                  95

Gly Gly Leu Gly Asp Val Leu Gly Gly Leu Pro Pro Ala Leu Ala
                100                 105                 110
```

(2) INFORMATION FOR SEQ ID NO:19:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1..43
        (D) OTHER INFORMATION: /note= "Amino acid sequence encoded
            by nucleotides 3817-3945 of SEQ ID NO. 5."

(xi) SEQUENCE DESCRIPTION: SEQ ID NO:19:

```
Cys Asp Val Val Asp Pro Ala Asp Val Leu Lys Ile Val Thr Thr Val
1               5                   10                  15

Ala Arg Ala Leu Ala Val Tyr Gly Thr Leu Ala Phe Ala Glu Met Ile
                20                  25                  30

Lys Asn Cys Met Ser Glu Glu Leu Ser Trp Lys
                35                  40
```

(2) INFORMATION FOR SEQ ID NO:20:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1..38
        (D) OTHER INFORMATION: /note= "Amino acid sequence encoded
            by nucleotides 4031-4144 of SEQ ID NO. 5."

(xi) SEQUENCE DESCRIPTION: SEQ ID NO:20:

```
Glu Pro Ala Lys Lys Trp Glu Thr Leu Leu Leu Gly Leu Gly Ala Ser
1               5                   10                  15

Gly Ser Glu Pro Gly Val Glu Gly Glu Ile Ala Pro Leu Ala Lys
                20                  25                  30

Glu Asn Val Ala Thr Pro
            35
```

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear -continued

```
(ii) MOLECULE TYPE: RNA (ix) FEATURE:
    (A) NAME/KEY: misc_RNA
    (B) LOCATION: 1
    (D) OTHER INFORMATION: /note= "Nucleotide 1 is a 7-methyl
        guanine added by 5'-5' linkage as an RNA cap."

(xi) SEQUENCE DESCRIPTION: SEQ ID NO:21:

GAUGGCAAGA AAAAAAA                                                         17
```

GENETICALLY ENGINEERED MODIFICATION OF POTATO TO FORM AMYLOPECTIN-TYPE STARCH

This application is a 371 of PCT/SE91/00892 filed 20 Dec. 1991.

The present invention relates to genetically engineered modification of potato, resulting in the formation of practically solely amylopectin-type starch in the potato. The genetically engineered modification implies the insertion of gene fragments into potato, said gene fragments comprising parts of leader sequence, translation start, translation end and trailer sequence as well as coding and noncoding (i.e. exons and introns) parts of the gene for granule-bound starch synthase, inserted in the antisense direction.

BACKGROUND OF THE INVENTION

Starch in various forms is of great import in the food and paper industry. In future, starch will also be a great potential for producing polymers which are degradble in nature, e.g. for use as packing material. Many different starch products are known which are produced by derivatisation of native starch originating from, inter alia, maize and potato. Starch from potato and maize, respectively, is competing in most market areas.

In the potato tuber, starch is the greatest part of the solid matter. About ¼ to ⅕ of the starch in potato is amylose, while the remainder of the starch is amylopectin. These two components of the starch have different fields of application, and therefore the possibility of producing either pure amylose or pure amylopectin is most interesting. The two starch components can be produced from common starch, which requires a number of process steps and, consequently, is expensive and complicated.

It has now proved that by genetic engineering it is possible to modify potato so that the tubers merely produce mainly starch of one or the other type. As a result, a starch quality is obtained which can compete in the areas where potato starch is normally not used today. Starch from such potato which is modified in a genetically engineered manner has great potential as a food additive, since it has not been subjected to any chemical modification process.

Starch Synthesis

The synthesis of starch and the regulation thereof are presently being studied with great interest, both on the level of basic research and for industrial application. Although much is known about the assistance of certain enzymes in the transformation of saccharose into starch, the biosynthesis of starch has not yet been elucidated. By making researches above all into maize, it has, however, been possible to elucidate part of the ways of synthesis and the enzymes participating in these reactions. The most important starch-synthesising enzymes for producing the starch granules are the starch synthase and the branching enzyme. In maize, three forms of starch synthase have so far been demonstrated and studied, two of which are soluble and one is insolubly associated with the starch granules. Also the branching enzyme consists of three forms which are probably coded by three different genes (Mac Donald & Preiss, 1985; Preiss, 1988).

The Waxy Gene in Maize

The synthesis of the starch component amylose essentially occurs by the action of the starch synthase alpha-1,4-D-glucane-4-alpha-glucosyl transferase (EC 2.4.1.21) which is associated with the starch granules in the growth cell. The gene coding for this granule-bound enzyme is called "waxy" (=$wx^+$), while the enzyme is called "GBSS" (granule-bound starch synthase).

Waxy locus in maize has been thoroughly characterised both genetically and biochemically. The waxy gene on chromosome 9 controls the production of amylose in endosperm, pollen and the embryo sac. The starch formed in endosperm in normal maize with the $wx^+$ allele consists to 25% of amylose and to 75% of amylopectin. A mutant form of maize has been found in which the endosperm contains a mutation located to the $wx^+$ gene, and therefore no functioning GBSS is synthesised. Endosperm from this mutant maize therefore contains merely amylopectin as the starch component. This so-called waxy mutant thus contains neither GBSS nor amylose (Echt & Schwartz, 1981).

The GBSS protein is coded by the $wx^+$ gene in the cell nucleus but is transported to and active in the amyloplast. The preprotein therefore consists of two components, viz. a 7 kD transit peptide which transfers the protein across the amyloplast membrane, and the actual protein which is 58 kD. The coding region of the $wx^+$ gene in maize is 3.7 kb long and comprises 14 exons and 13 introns. A number of the regulation signals in the promoter region are known, and two different polyadenylating sequences have been described (Klösgen et al, 1986; Schwartz-Sommer et al, 1984; Shure et al, 1983).

Amylose Enzyme in Potato

In potato, a 60 kD protein has been identified, which constitutes the main granule-bound protein. Since antibodies against this potato enzyme cross-react with GBSS from maize, it is assumed that it is the granule-bound synthase (Vos-Scheperkeuter et al, 1986)., The gene for potato GBSS has, however, so far not been characterised to the same extent as the waxy gene in maize, either in respect of locating or structure.

Naturally occurring waxy mutants have been described for barley, rice and sorghum besides maize. In potato no natural mutant has been found, but a mutant has been produced by X-radiation of leaves from a monohaploid (n=12) plant (Visser et al, 1987). Starch isolated from tubers of this mutant contains neither the GBSS protein nor amylose. The mutant is conditioned by a simple recessive gene and is called amf. It may be compared to waxy mutants of other plant species since both the GBSS protein and amylose are lacking. The stability of the chromosome number, however, is weakened since this is quadrupled to the natural number (n=48), which can give negative effects on the potato plants (Jacobsen et al, 1990).

Inhibition of Amylose Production

The synthesis of amylose can be drastically reduced by inhibition of the granule-bound starch synthase, GBSS, which catalyses the formation of amylose. This inhibition results in the starch mainly being amylopectin.

Inhibition of the formation of enzyme can be accomplished in several ways, e.g. by:

mutagen treatment which results in a modification of the gene sequence coding for the formation of the enzyme incorporation of a transposon in the gene sequence coding for the enzyme genetically engineered modification so that the gene coding for the enzyme is not expressed, e.g. antisense gene inhibition.

FIG. 1 illustrates a specific suppression of normal gene expression in that a complementary antisense nucleotide tide is allowed to hybridise with mRNA for a target gene.

The antisense nucleotide thus is antisense RNA which is transcribed in vivo from a "reversed" gene sequence (Izant, 1989).

By using the antisense technique, various gene functions in plants have been inhibited. The antisense construct for chalcone synthase, polygalacturonase and phosphinotricin acetyltransferase has been used to inhibit the corresponding enzyme in the plant species petunia, tomato and tobacco.
Inhibition of Amylose in Potato In potato, experiments have previously been made to inhibit the synthesis of the granule-bound starch synthase (GBSS protein) with an antisense construct corresponding to the gene coding for GBSS (this gene is hereinafter called the "GBSS gene"). Hergersberger (1988) describes a method by which a cDNA clone for the GBSS gene in potato has been isolated by means of a cDNA clone for the $wx^+$ gene in maize. An antisense construct based on the entire CDNA clone was transferred to leaf discs of potato by means of Agrobacterium tumefaclens. In microtubers induced in vitro from regenerated potato sprouts, a varying and very weak reduction of the amylose content was observed and shown in a diagram. A complete characterisation of the GBSS gene is not provided.

The gene for the GBSS protein in potato has been further characterised in that a genomic wx clone was examined by restriction analysis. However, the DNA sequence of the clone has not been determined (Visser et al, 1989).

Further experiments with an antisense construct corresponding to the GBSS gene in potato have been reported. The antisense construct which is based on a cDNA clone together with the CaMV 35S promoter has been transformed by means of Agrobacterium rhizogenes. According to information, the transformation resulted in a lower amylose content in the potato, but no values have been accounted for (Flavell, 1990).

None of the methods used so far for genetically engineered modification of potato has resulted in potato with practically no amylose-type starch.

The object of the invention therefore is to provide a practically complete suppression of the formation of amylose in potato tubers.

SUMMARY OF THE INVENTION

According to the invention, the function of the GBSS gene and, thus, the amylose production in potato are inhibited by using completely new antisense constructs. For forming the antisense fragments according to the invention, the genomic GBSS gene is used as a basis in order to achieve an inhibition of GBSS and, consequently, of the amylose production, which is as effective as possible. The antisense constructs according to the invention comprise both coding and noncoding parts of the GBSS gene which correspond to sequences in the region comprising promoter as well as leader sequence, translation start, translation end and trailer sequence in the antisense direction. For a tissue-specific expression, i.e. the amylose production should be inhibited in the potato tubers only, use is made of promoters which are specifically active in the potato tuber. As a result, the starch composition in other parts of the plant is not affected, which otherwise would give negative side-effects.

The invention thus comprises a fragment which essentially has one of the nucleotide sequences stated in SEQ ID No. 1, SEQ ID No. 2 or SEQ ID No. 3. However, the sequences may deviate from those stated by one or more non-adjacent base pairs, without affecting the function of the fragments.

The invention also comprises a potato-tuber-specific promoter comprising 987 bp which belongs to the gene according to the invention, which codes for granule-bound starch synthase. Neither the promoter nor the corresponding gene has previously been characterised. The promoter sequence of 987 bp is stated in SEQ ID No. 4, while the gene sequence is stated in SEQ ID No. 5. Also the promoter and gene sequences may deviate from those stated by one or more non-adjacent base pairs, without affecting their function.

The invention also comprises vectors including the antisense fragments and the antisense constructs according to the invention.

In other aspects the invention comprises cells, plants, tubers, microtubers and seeds whose genome contains the fragments according to the invention inserted in the antisense direction.

In still further aspects, the invention comprises amylopectin-type starch, both native and derivatised.

Finally, the invention comprises a method of suppressing amylose formation in potato, whereby mainly amylopectin-type starch is formed in the potato.

Moreover, the sequences of the different DNA fragments according to the invention are shown in SEQ ID Nos 1, 2, 3, 4 and 5. There may be deviations from these sequences in one or more non-adjacent base pairs.

DETAILED DESCRIPTION OF THE INVENTION

Materials

In the practical carrying out of the invention the following materials were used:
Bacterial Strains E. coli DH5alfa and DH5alfaF'IQ(BRL). E. coli JM105 (Pharmacia). A. tumefaciens LBA4404 (Clontech).
Vectors M13mpl8 and mp19 (Pharmacia). pBI101 and pBI121 (Clontech). pBI240.7 (M. W. Bevan). pUC plasmids (Pharmacia).
Enzymes Restriction enzymes and EcoRI linker (BRL). UNION™ DNA Ligation Kit (Clontech). Sequenase• DNA Sequencing Kit (USB). $T_4$-DNA ligase (Pharmacia).

The above-mentioned materials are used according to specifications stated by the manufacturers.
Genomic Library A genomic library in EMBL3 has been produced by Clontech on the applicant's account, while using leaves of the potato Bintje as starting material.
Identification and Isolation of the GBSS Gene The genomic library has been screened for the potato GBSS gene by means of cDNA clones for both the 5' and 3' end of the gene (said cDNA clones being obtained from M Hergersberger, Max Plank Institute in Cologne) according to a protocol from Clontech.

A full-length clone of the potato CBSS gene, wx311, has been identified and isolated from the genomic library. The start of the GBSS gone has been determined at an EcoRI fragment which in called fragment w (3.95 kb). The end of the GBSS gene has also been datrind at an ECORI fragment which in called fragment x (5.0 kb). BglII-SpeI fragment which is called fragment m (3.9 kb) has also been isolated and shares sequences both from fragment w and from fragment x. The fragments w, m and x have been subcloned in pUC13 (Viera, 1982, Yanisch-Paron at el, 1985) and are called pSw, pSn and pSx, respectively (FIG. 2).

Characterisation of the GBSS Gene in Potato

Figure 1:
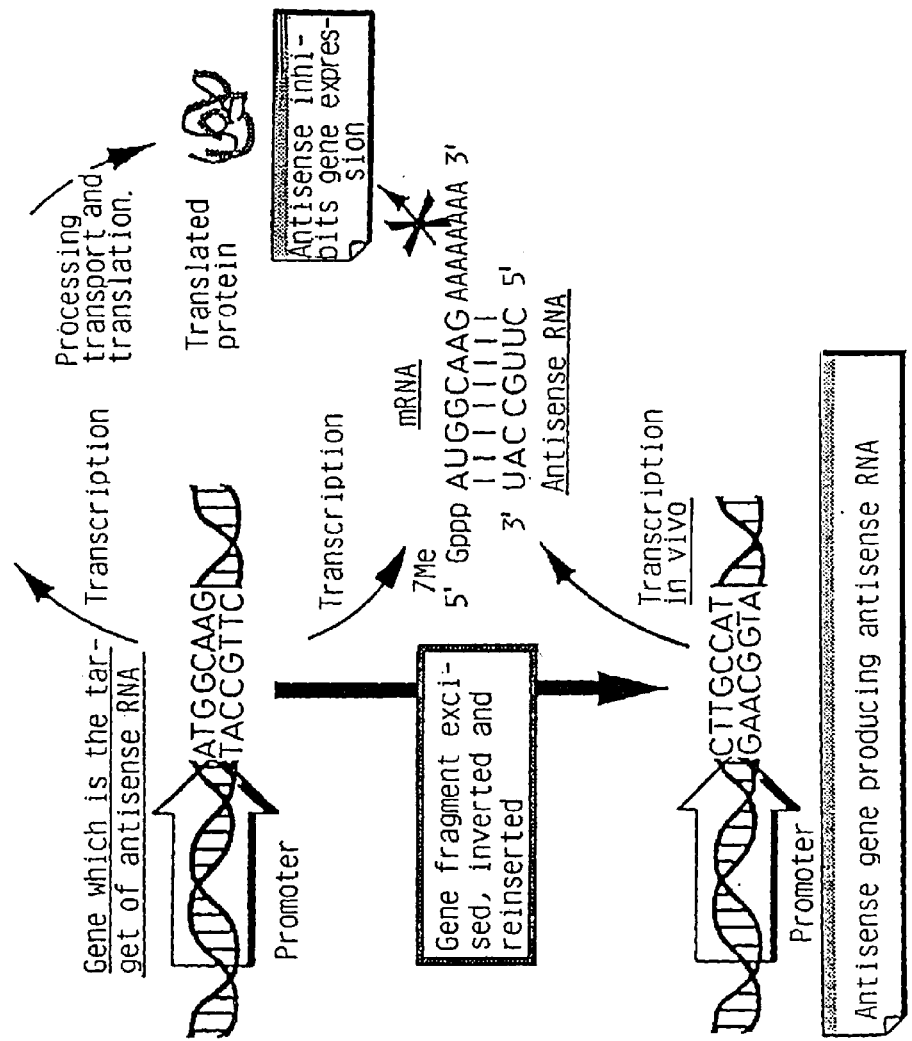
FIG. 1 illustrates the principle of the antisense ene inhibition [SEQ ID No. 21].
Figure 2:
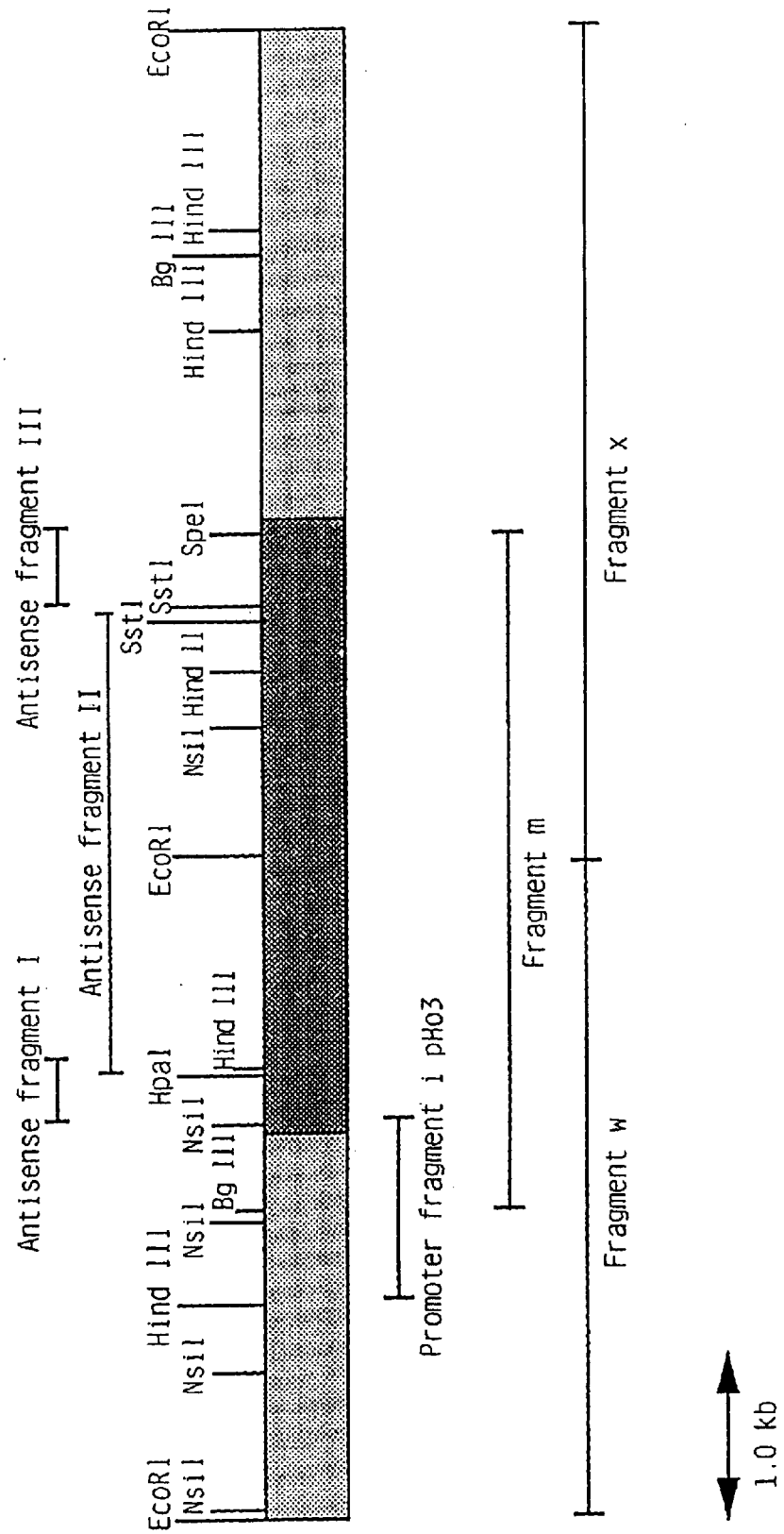
FIG. 2 shows the result of restriction analysis of the potato GBSS gene.

The GBSS gene in potato has been characterised by restriction analysis and cDNA probes, where the 5' and 3' end of the GBSS gene has been determined more accurately (FIG. 2). Seuence determination according to Sangar et al, 1977 of the GBSS gene has been made on subclones from pSw and pSx in M13mpl8 and mpl9 as well as pUC19 starting eround the 5' end (see SEQ ID No. 5).

The promoter region has beon determined at a BglII-NsiI fr nt (see SEQ ID No. 4). Transcription and translation start has been determined at an overlapping BglII-HindIII fragment. The terminator region has in turn been determined at a SpeI-HindIII fragment.

Antisense Constructs for the GBSS Gene in Potato

The HBSS gene fragments according to the invention (see SEQ ID Nos 1, 2 and 3. and FIG. 2) have been determined in the following manner.

The restriction of pSw with NsiI and HindIII gives fragment I (SEQ ID NO. 1) which subcloned in pUC19 is called 19NH35. Further restriction of 19 NH35 with HpaI-SstI gives a fragment containing 342 bp of the GBSS gene according to the invention. This fragment comprises leader sequence, translation start and the first 125 bp of the coding region.

The restriction of pSm with HpaI and NsiI gives fragment II (SEQ ID No. 2) which subcloned in pJRD184 (Heusterspreute et al, 1987) is called pJRDmitt. Further restriction of pJRDmitt with HpaI-SstI gives a fragment containing 2549 bp of the GBSS gene according to the invention. This fragment comprises exons and introns from the middle of the gene.

The restriction of pSx with SstI and SpeI gives fragment III (SEQ ID No. 3) which subcloned in pBluescript (Melton et al, 1984) is called pBlue3'. Further restriction of pBlue3' with BamHI-SstI gives a fragment containing ing 492 bp of the GBSS gene according to the invention.

This fragment comprises the last intron and exon, translation end and 278 bp of trailer sequence.

Figure 4:
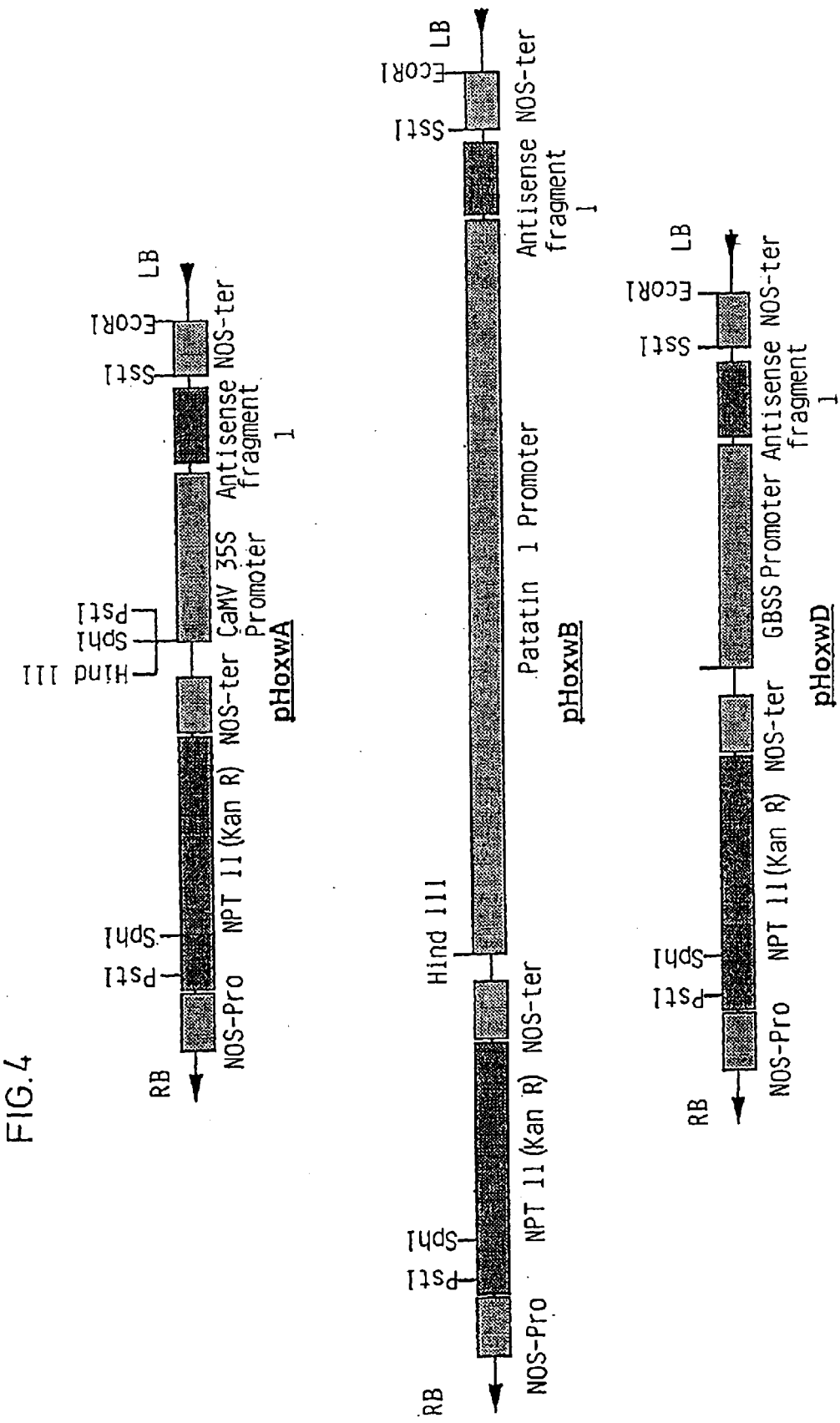
FIG. 4 shows the antisense constructs pHoxwA, pHoxwB and pHoxwD.

Antisense Constructs with Fragment I (FIG. 4)

For the antisense construct pHoxwA, the HpaI-SstI fragment from 19NH35 has been inserted in the antisense direction into the binary vector pBI121 (Jefferson et al, 1987) cleaved with SmaI-SstI. The transcription of the antisense fragment is then initiated by the CaMV 35S promoter and is terminated by the NOS terminator (NOS= nopaline synthase).

Figure 3:
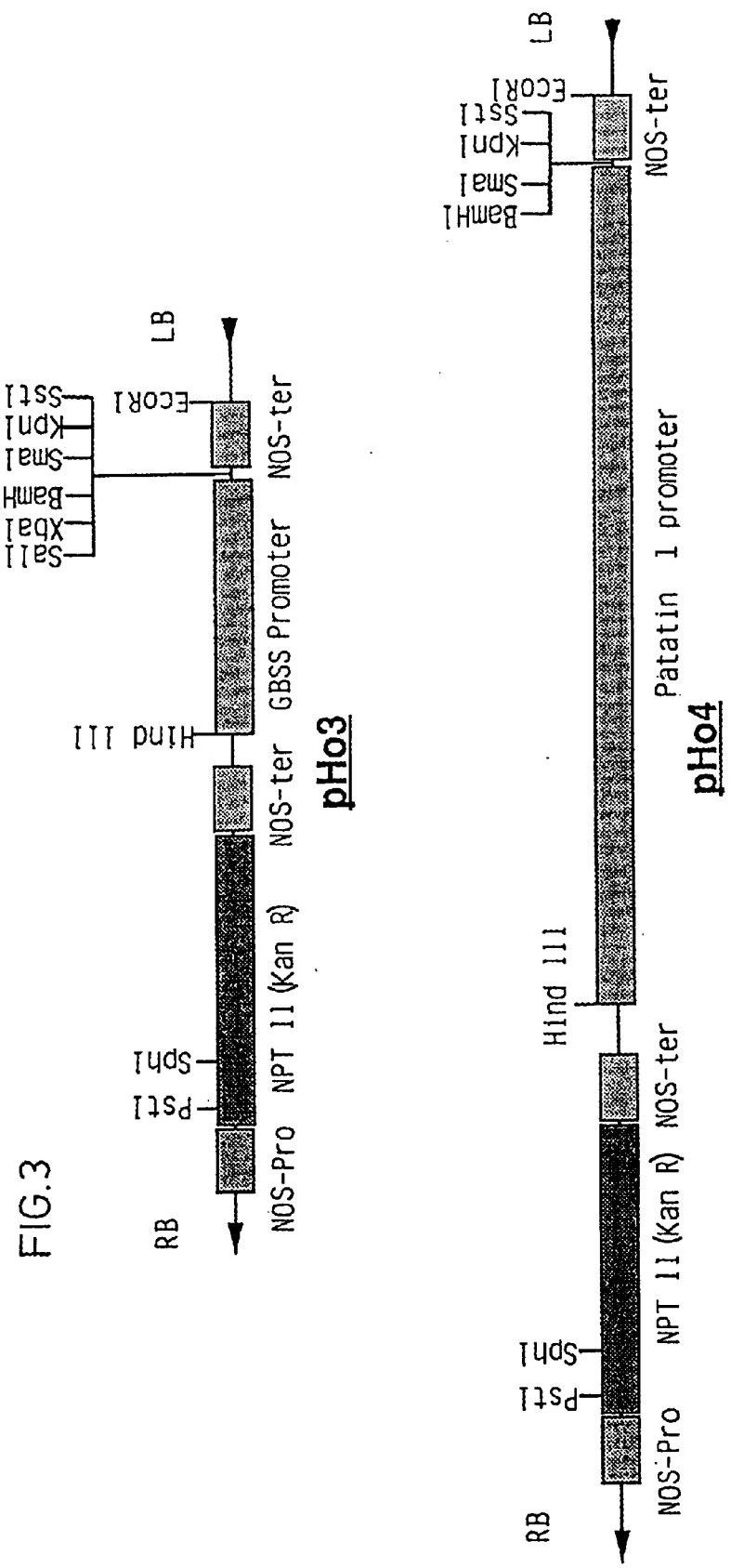
FIG. 3 shows two new binary vectors pHo3 and pHo4.

For the antisense construct pHoxwB, the HpaI-SstI fragment from 19NH35 has been inserted in the antisense direction into the binary vector pHo4 (FIG. 3) cleaved with SmaI-SstI. The patatin I promoter which is tuber specific in potato comes from the vector pBI240.7 obtained from M. Bevan, Institute of Plant Science Research, Norwich. The transcription of the antisense fragment is then initiated by the patatin I promoter and is terminated by the NOS terminator.

For the antisense construct pHoxwD, the HpaI-SstI fragment from 19NH35 has been inserted in the antisense direction into the binary vector pHo3 (FIG. 3) cleaved with SmaI-SstI. pHo3 is a new binary vector which is constructed on the basis of pBI101. This vector which contains the promoter according to the invention (see SEQ ID No. 4) (GBSS promoter) of the now characterised potato GBSS gene according to the invention has been restriction-cleaved with SmaI and SstI, the HpaI-SstI fragment from 19NH35 being inserted in the antisense direction. The transcription of the antisense fragment is then initiated by its own GBSS promoter and is terminated by the NOS terminator. This means that the antisense fragment is transcribed only in the potato tuber, since the GBSS promoter like the patatin I promoter is tuber-specific.

Figure 5:
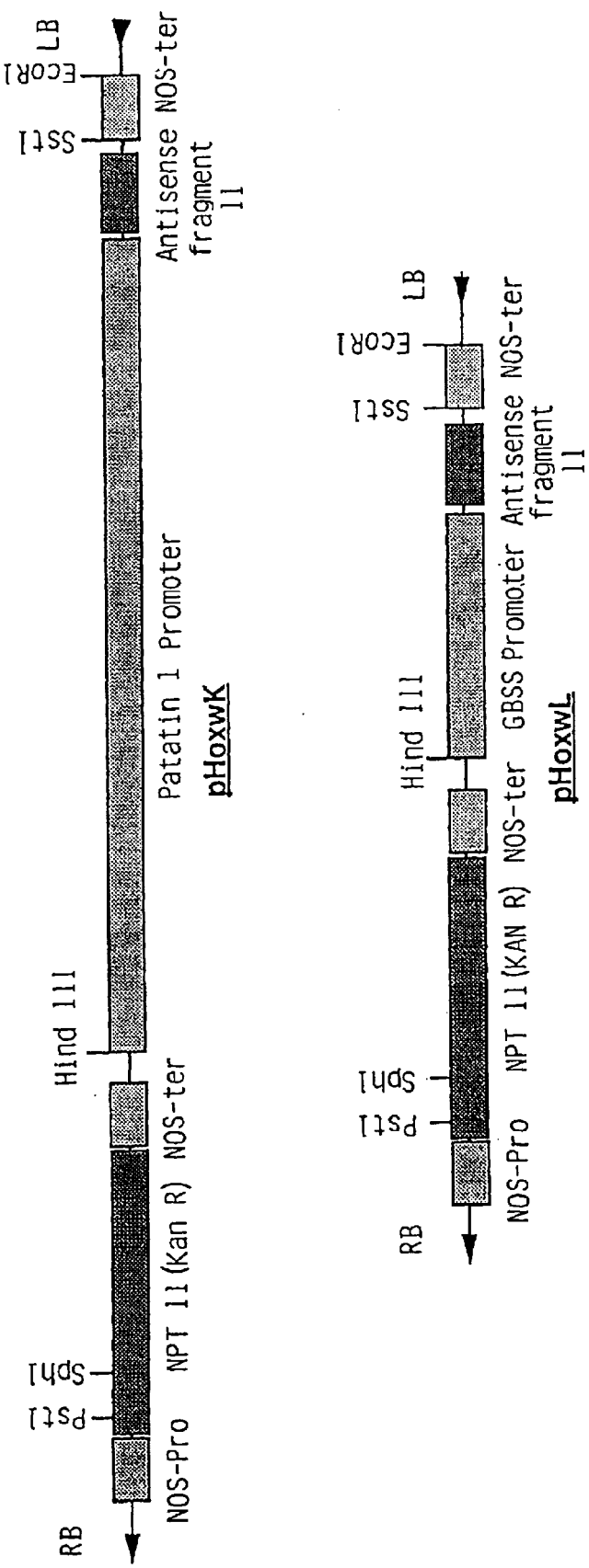
FIG. 5 shows the antisense constructs pHoxwF and pHoxwG.

Antisense Constructs with Fragment II (FIG. 5)

For the antisense construct pHoxwF, the HpaI-SstI fragment from pJRDmitt has been inserted in the antisense direction into the binary vector pHo4 cleaved with SmaI-SstI. The transcription of the antisense fragment is then initiated by the patatin I promoter and terminated by the NOS terminator.

For the antisense construct pHoxwG, the HpaI-SstI fragment from pJRDmitt has been inserted in the antisense direction into the binary vector pHo3 cleaved with SmaI-SstI. The transcription of the antisense fragment is then initiated by its own GBSS promoter and is terminated by the NOS terminator.

Figure 6:
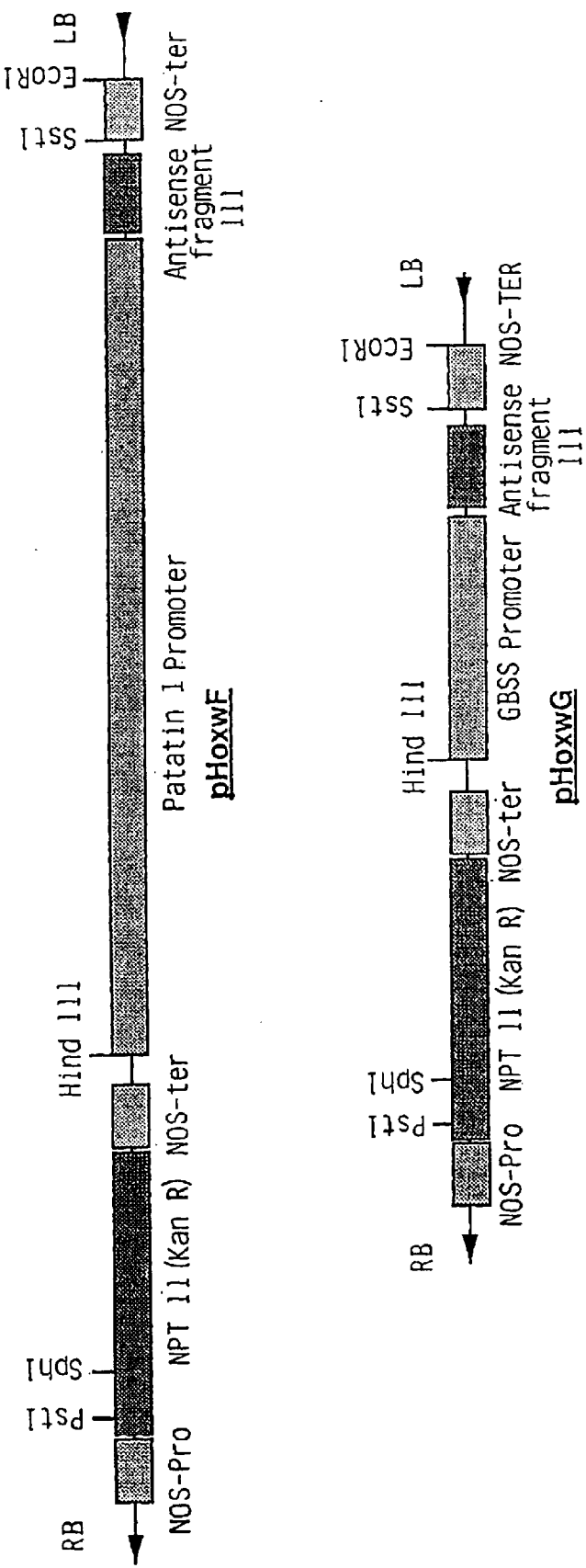
FIG. 6 shows the antisense constructs pHoxwK and pHoxwL.

Antisense Constructs with Fragment III (FIG. 6)

For the antisense construct pHoxwK, the BamHI-SstI fragment from pBlue3' has been inserted in the antisense direction into the binary vector pHo4 cleaved with BamHI-SstI. The transcription of the antisense fragment is then initiated by the patatin I promoter and is terminated by the NOS terminator.

For the antisense construct pHoxwL, the BamHI-SstI fragment from pBlue3' has been inserted in the antisense direction into the binary vector pHo3 cleaved with BamHI-SstI. The transcription of the antisense fragment is then initiated by its own GBSS promoter and is terminated by the NOS terminator.

The formed antisense contructs (FIGS. 4, 5, 6) have been transformed to Agrobacterium tumefaciens strain LBA4404 by direct transformation with the "freeze-thawing" method (Hoekema et al, 1983, An et al, 1988).

Transformation

The antisense constructs are transferred to bacteria, suitably by the "freeze-thawing" method (An et al, 1988). The transfer of the recombinant bacterium to potato tissue occurs by incubation of the potato tissue with the recombinant bacterium in a suitable medium after some sort of damage has been inflicted upon the potato tissue. During the incubation, T-DNA from the bacterium enters the DNA of the host plant. After the incubation, the bacteria are killed nd the potato tissue is transferred to a solid medium for callus induction and is incubated for growth of callus.

After pausing through further suitable media, sprouts are formed which are cut away from the potato tissue.

Checks for testing the expression of the antisense constructs and the transfer thereof to the potato genome are carried out by e.g. southern snd northern hybridisation (Manatis et al (1982)). The number of copies of the antisense construct which has been transferred is determined by southern hybridisation.

The testing of the expression on protein level is suitably carried out on microtubers induced in vitro on the transformed sprouts, thus permitting the testing to be performed an quickly as possible.

Characterisation of the GBSS Protein

The effect of the antisense constructs on the function of the GBSS gene with respect to the activity of the GBSS protein is examined by extracting starch from the microtubers and analysing it regarding the presence of the GBSS protein. In electrophoresis on polyacrylamide gel (Hovenkamp-Hermelink et al, 1987), the GBSS protein forms a distinct band at 60 kD. when the GBSS gene functions. When the GBBS gene is not expressed, i.e. when the antisense GBSS gene is fully expressed, thereby inhibiting the formation of GBSS protein, no 60 kD band is demonstrated on the gel.

Characterisation of the Starch

The composition of the starch in microtubers is identical with that of ordinary potato tubers, and therefore the effect of the antisense constructs on the amylose production is examined in microtubers. The proportion of amylose to amylopectin can be determined by a spectrophotometric method (e.g. according to Hovenkamp-Hermelink et al, 1988).

Extraction of Amylopectin from Amylopectin Potato

Amylopectin is extracted from the so-called amylopectin potato (potato in which the formation of amylose has been suppressed by inserting the antisense constructs according to the invention) in a known manner.

Derivatisation of Amylopectin

Depending on the final use of the amylopectin, its physical and chemical qualities can be modified by derivatisation. By derivatisation is here meant chemical, physical and enzymatic treatment and combinations thereof (modified starches).

The chemical derivatisation, i.e. chemical modification of the amylopectin, can be carried out in different ways, for example by oxidation, acid hydrolysis, dextrinisation, different forms of etherification, such as cationisation, hydroxy propylation and hydroxy ethylation, different forms of esterification, for example by vinyl acetate, acetic anhydride, or by monophosphatising, diphosphatising and octenyl succination, and combinations thereof.

Physical modification of the amylopectin can be effected by e.g. cylinder-drying or extrusion.

In enzymatic derivatisation, degradation (reduction of the viscosity) and chemical modification of the amylopectin are effected by means of existing enzymatic systems.

The derivatisation is effected at different temperatures, tures, according to the desired end product. The ordinary range of temperature which is used is 20–45° C., but temperatures up to 180° C. are possible.

The invention will be described in more detail in the following Examples.

EXAMPLE 1

Production of Microtubers with Inserted Antisense Constructs According to the Invention The antisense constructs (see FIGS. 4, 5 and 6) are transferred to Agrobacterium tumefaciens LBA 4404 by the "freeze-thawing" method (An et al, 1988). The transfer to potato tissue is carried out according to a modified protocol from Rocha-Sosa et al (1989).

Leaf discs from potato plants cultured in vitro are incubated in darkness on a liquid MS-medium (Murashige & Skoog; 1962) with 3% saccharose and 0.5% MES together with 100 µl of a suspension of recombinant Agrobacterium per 10 ml medium for two days. After these two days the bacteria are killed. The leaf discs are transferred to a solid medium for callus induction and incubated for 4–6 weeks, depending on the growth of callus. The solid medium is composed as follows:

| MS + 3% saccharose | |
|---|---|
| 2 mg/l | zeatin riboside |
| 0.02 mg/l | "NAA" |
| 0.02 mg/l | "GA$_3$" |
| 500 mg/l | "Claforan" |
| 50 mg/l | kanamycin |
| 0.25% | "Gellan" |

Subsequently the leaf discs are transferred to a medium having a different composition of hormones, comprising:

| MS + 3% saccharose | |
|---|---|
| 5 mg/l | "NAA" |
| 0.1 mg/l | "BAP" |
| 500 mg/l | "Claforan" |
| 50 mg/l | kanamycin |
| 0.25% | "Gellan" |

The leaf discs are stored on this medium for about 4 weeks, whereupon they are transferred to a medium in which the "Claforan" concentration has been reduced to 250 mg/l. If required, the leaf discs are then moved to a fresh medium every 4 or 5 weeks. After the formation of sprouts, these are cut away from the leaf discs and transferred to an identical medium.

The condition that the antisense construct has been transferred to the leaf discs is first checked by analysing leaf extracts from the regenerated sprouts in respect of glucuronidase activity by means of the substrates described by Jefferson et al (1987). The activity is demonstrated by visual assessment.

Further tests of the expression of the antisense constructs and the transfer thereof to the potato genome are carried out by southern and northern hybridisation according ing to Maniatis et al (1981). The number of copies of the antisense constructs that has been transferred is determined by southern hybridisation.

When it has been established that the antisense constructs have been transferred to and expressed in the potato genome, the testing of the expression on protein level begins. The testing is carried out on microtubers which have been induced in vitro on the transformed sprouts, thereby avoiding the necessity of waiting for the development of a complete potato plant with potato tubers.

Stem pieces of the potato sprouts are cut off at the nodes and placed on a modified MS medium. There they form 35 microtubers after 2–3 weeks in incubation in darkness at 19° C. (Bourque et al, 1987). The medium is composed as follows:

| MS + 6% saccharose |
|---|
| 2.5 mg/l kinetin |
| 2.5 mg/l "Gellan" |

The effect of the antisense constructs on the functions of the GBSS gene in respect of the activity of the GBSS protein is analysed by means of electrophoresis on polyacrylamide gel (Hovenkamp-Hermelink et al, 1987). Starch is extracted from the microtubers and analysed regarding the presence of the GBSS protein. In a polyacrylamide gel, the GBSS protein forms a distinct band at 60 kD, when the GBSS gene functions. If the GBSS gene is not expressed, i.e. when the antisense GBSS gene is fully expressed so that the formation of GBSS protein is inhibited, no 60 kD band can be seen on the gel.

The composition of the starch, i.e. the proportion of amylose to amylopectin, is determined by a spectrophotometric method according to Hovenkamp-Hermelink et al (1988), the content of each starch component being determined on the basis of a standard graph.

EXAMPLE 2
Extraction of Amylopectin from Amylopectin Potato

Potato whose main starch component is amylopectin, below called amylopectin potato, modified in a genetically engineered manner according to the invention, is grated, thereby releasing the starch from the cell walls.

The cell walls (fibres) are separated from fruit juice and starch in centrifugal screens (centrisiler). The fruit juice is separated from the starch in two steps, viz. first in hydrocyclones and subsequently in specially designed band-type vacuum filters.

Then a finishing refining is carried out in hydrocyclones in which the remainder of the fruit juice and fibres are separated.

The product is dried in two steps, first by predrying on a vacuum filter and subsequently by final drying in a hot-air current.

EXAMPLE 3
Chemical Derivatisation of Amylopectin

Amylopectin is sludged in water to a concentration of 20–50%. The pH is adjusted to 10.0–12.0 and a quatenary ammonium compound is added in such a quantity that the end product obtains a degree of substitution of 0.004–0.2. The reaction temperature is set at 20–45° C. When the reaction is completed, the pH is adjusted to 4–8, whereupon the product is washed and dried. In this manner the cationic starch derivative 2-hydroxy-3-trimethyl ammonium propyl ether is obtained.

EXAMPLE 4
Chemical Derivatisation of Amylopectin

Amylopectin is sludged in water to a water content of 10–25% by weight. The pH is adjusted to 10.0–12.0, and a quatenary ammonium compound is added in such a quantity that the end product obtains a degree of substitution of 0.004–0.2. The reaction temperature is set at 20–45° C. When the reaction is completed, the pH is adjusted to 4–8. The end product is 2-hydroxy-3-trimethyl ammonium propyl ether.

EXAMPLE 5
Chemical Derivatisation of Amylopectin

Amylopectin is sludged in water to a concentration 25 of 20–50% by weight. The pH is adjusted to 5.0–12.0, and sodium hypochlorite is added so that the end product obtains the desired viscosity. The reaction temperature is set at 20–45° C. When the reaction is completed, the pH is adjusted to 4–8, whereupon the end product is washed and dried. In this manner, oxidised starch is obtained.

EXAMPLE 6
Physical Derivatisation of Amylopectin

Amylopectin is sludged in water to a concentration of 20–50% by weight, whereupon the sludge is applied to a heated cylinder where it is dried to a film.

EXAMPLE 7
Chemical and Physical Derivatisation of Amylopectin

Amylopectin is treated according to the process described in one of Examples 3–5 for chemical modification and is then further treated according to Example 6 for physical derivatisation.

References

Mac Donald, F. D. and Preiss, J., 1985, Plant. Physiol.o 78:849–852

Preiss, J., 1988, In The Biochemistry of Plants 14 (Carbohydrates). Ed. J. Preiss, Academic Press; 181–254

Echt, C. S. and Schwarz, D., 1981, Genetics 99:275–284

Klösgen, R. B., Gierl, A., Schwarz-Sommer, Z. and Saedler, H., 1986, Mol. Gen. Genet. 203:237–244

Schwarz-Sommer, Z., Gierl, A., Klösgen, R. B., Wienand, U., Peterson, P. A. and Saedler, H., 1984, EMBO J. 3(5):1021–1028

Shure, M., Wessler, S. and Fedoroff, N., 1983, Cell 35:225–233

Jacobsen, E., Kriggsheld, H. T., Hovenkamp-Hermelink, J. H. M., Ponstein, A. S., Witholt, B. and Feenstra, W. J., 1990, Plant. Sci. 67:177–182

Visser, R. G. F., Hovenkamp-Hermelink, J. H. M., Ponstein, A. S., Vos-Scheperkeuter, G. H., Jacobsen, E., Feenstra, W. J. and Witholt, B., 1987, Proc. 4th European Congress on Biotechnology 1987, Vol. 2, Elsevier, Amsterdam; 432–435

Vos-Scheperkeuter, G. H., De Boer, W., Visser, R. G. F., Feenstra, W. J. and Witholt, B., 1986, Plant. Physiol. 82:411–416

Cornelissen, M., 1989, Nucleic Acids Res. 17(18): 7203–7209

Izant, J. G., 1989, Cell Motility and Cytosceleton 14:81–91

Sheehy; R. E., Kramer, M., Hiatt, W. R., 1988, Proc. Natl. Acad. Sci. USA, 85(23):8805–8809

Van der Krol, A. R., Mur, L. A., de Lange, P., Gerats, A. G. M., Mol, J. N. M. and Stuitje, A. R., 1960, Mol. Gen. Genet. 220:204–212

Flavell, R. B., 1990, AgBiotech. News and Information 2(5):629–630

Hergersberger, M., 1988, Molekulare Analyse des waxy Gens aus Solanum tuberosum und Expression von waxy antisense RNA in transgenen Kartoffeln. Thesis for a doctorate from the University in Cologne Visser, R. G. F., Hergersberger, M., van der Leij, F. R., Jacobsen, E., Witholt, B. and Feenstra, W. J., 1989, Plant. Sci. 64:185–192

An, G., Ebert, P. R., Mitra, A. and Ha, S. B., 1987, Plant Mol. Biol. Manual A3:1–19

Hoekema, A., Hirsch, P. R., Hooykaas, P. J. J. and Schilperoort, R. A., 1983, Nature 303:179–180

Jefferson, R. A., Kavanagh, T. A. and Bevan, M. W., 1987, EMBO J. 6:3201–3207

Sanger, F., Nicklen, S. and Coulson, A. R., 1977, Proc. Natl. Acad. Sci. USA 74:5463–5467

Viera, J. and Messing, J., 1982, Gene 19:259–268

Yanisch-Perron, C., Viera, J. and Messing, J., 1985, Gene 33:103–119

Heusterspreute et al (1987) Gene 53:294–300

Melton, D. A. et al (1984), Nucleic Acids Res. 12:7035–7056 (the plasmide is sold by Stratagene)

Murashige, T. and Skoog, F., 1962, Physiol. Plant 15:473–497.

Rocha-Sosa, M., Sonnewald, U., Frommer, W., Stratmann, M., Shell, J. and Willmitzer, L., 1989, EMBO J., 8(1): 23–29

Jefferson, R. A., Kavanagh, R. A. and Bevan, M. W., 1987, EMBO J. 6:3901–3907

Maniatis, T., Fritsch, E. F. and Sambrook, J., 1982, Molecular Cloning, A Laboratory Handbook, Cold Spring Harbor Laboratory Press, Cold Spring Harbor Bourque, J. E., Miller, J. C. and Park, W. D., 1987, In Vitro Cellular & Development Biology 23(5):381–386

Hovenkamp-Hermelink, J. H. M., Jacobsen, E., Ponstein, A. S., Visser, R. G. F., Vos-Scheperkeuter, G. H., Bijmolt, E. W., de Vries, J. N., Witholt, B. J. & Feenstra, W. J., 1987, Theor. Appl. Genet. 75:217–221

Hovenkamp-Hermelink, J. H. M., de Vries, J. N., Adamse, P., Jacobsen, E., Witholt, B. and Feenstra, W. J., 1988, Potato Research 31:241–246

Modified starches: Properties and use D. B. Wurzburg

Bevan, M. W., 1984. Nucleic Acids Res. 12:8711–8721.

---

What is claimed is:

1. A method of suppressing amylose formation in potato, comprising:
   introducing into the genome of a potato tissue a gene construct comprising:
   a fragment of a potato gene that encodes a granule-bound starch synthase (GBSS) positioned in an antisense orientation, wherein said fragment contains a nucleotide sequence selected from the group consisting of SEQ ID NO. 1, SEQ ID NO. 2, SEQ ID NO. 3, and nucleotide sequences encoding one or more of the amino acid sequences of SEQ ID NOs. 6–17, operably linked to
   a promoter.

2. An isolated fragment of a potato gene that encodes a granule bound starch synthase (GBSS), wherein said fragment contains a nucleotide sequence selected from the group consisting of SEQ ID NO. 1, SEQ ID NO. 3, and nucleotide sequences encoding one or more of the amino acid sequences of SEQ ID NOs. 6–17.

3. An antisense construct capable of inhibiting expression of a gene that encodes a starch synthase in potato, comprising
   a promoter; operably linked to
   a fragment of a potato gene that encodes a granule-bound starch synthase positioned in an antisense orientation, wherein said fragment contains a nucleotide sequence selected from the group consisting of SEQ ID NO. 1, SEQ ID NO. 2, SEQ ID NO. 3, and nucleotide sequences encoding one or more of the amino acid sequences of SEQ ID NOs. 6–17.

4. The antisense construct as claimed in claim 3, wherein the promoter is derived from the potato gene that encodes said granule-bound starch synthase (GBSS).

5. The antisense construct as claimed in claim 3, wherein the promoter is selected from the group consisting of SEQ ID No. 4, a CaMV 35S promoter and a patatin I promoter.

6. A vector comprising a fragment of a potato gene that encodes a granule-bound starch synthase (GBSS), wherein said fragment contains a nucleotide sequence selected from the group consisting of SEQ ID NO. 1, SEQ ID NO. 3, and nucleotide sequences encoding one or more of the amino acid sequences of SEQ ID NOs. 6–17, said nucleotide sequence positioned in an antisense orientation in relation to a promoter positioned upstream from said nucleotide sequenceand operably linked thereto.

7. A vector comprising the antisense construct as claimed in claim 3.

8. A cell of a potato plant whose genome comprises the antisense construct as claimed in claim 3.

9. A potato plant whose genome comprises the antisense construct as claimed in claim 3.

10. A potato tuber whose genome comprises the antisense construct as claimed in claim 3.

11. A seed from a potato plant, wherein the genome of said seed comprises the antisense construct as claimed in claim 3.

12. A microtuber of a potato whose genome comprises the antisense construct as claimed in claim 3.

13. A vector comprising the antisense construct as claimed in claim 4.

14. A cell of a potato plant whose genome comprises the antisense construct as claimed in claim 4.

15. A potato plant whose genome comprises the antisense construct as claimed in claim 4.

16. A potato tuber whose genome comprises the antisense construct as claimed in claim 4.

17. A method for tuber-specific expression of a gene product in a potato comprising:
    transforming said potato with a DNA molecule comprising an isolated promoter from a potato gene that encodes a granule-bound starch synthase (GBSS).

18. The antisense construct as claimed in claim 3, wherein the promoter contains the sequence of SEQ ID NO. 4.

19. A method for tuber-specific expression of a gene product in a potato comprising:
    transforming said potato with a DNA molecule comprising a promoter sequence from a potato gene that encodes a granule-bound starch synthase (GBSS), said promoter sequence containing the nucleotide sequence of SEQ ID NO. 4.

20. A method of suppressing amylose formation in potato, comprising:
    cultivating a potato containing a gene construct comprising a fragment of a potato gene that encodes a granule-bound starch synthase (GBSS) positioned in an antisense orientation, wherein said fragment contains the nucleotide sequence of SEQ ID NO. 1.

21. A method of suppressing amylose formation in potato, comprising:
    cultivating a potato containing a gene construct comprising a fragment of a potato gene that encodes a granule-bound starch synthase (GBSS) positioned in an antisense orientation, wherein said fragment contains a nucleotide sequence selected from the group consisting of SEQ ID NO. 1, SEQ ID NO. 2, SEQ ID NO. 3, and nucleotide sequences encoding one or more of the amino acid sequences of SEO ID NOs. 6–7.

22. An isolated fragment of a potato gene that encodes a granule-bound starch synthase (GBSS), wherein said fragment contains a nucleotide sequence selected from the group consisting of SEQ ID NO. 1, SEQ ID NO. 2, SEQ ID NO. 3.

23. An antisense construct that is capable of inhibiting expression of a potato gene that encodes a granule-bound starch synthase (GBSS) comprising:

a promoter, operably linked to
a fragment of the potato gene that encodes said granule-bound starch synthase positioned in an antisense orientation, wherein said fragment contains a nucleotide sequence selected from the group consisting of SEQ ID NO. 1, SEQ ID NO. 2, and SEQ ID NO. 3.

24. The antisense construct as claimed in claim 23, wherein the promoter contains the sequence of SEQ ID NO. 4.

25. The antisense construct as claimed in claim 23, wherein the promoter is selected from the group consisting of SEQ ID NO. 4, a CAMV 35S promoter and a patatin I promoter.

26. A vector comprising a fragment of a potato gene that encodes a granule-bound starch synthase (GBSS), wherein said fragment contains a nucleotide sequence selected from the group consisting of SEQ ID NO. 1, SEQ ID NO. 2, and SEQ ID NO. 3, and said nucleotide sequence is positioned in an antisense orientation in relation to a promoter positioned upstream from said nucleotide sequence and operably linked thereto.

27. A vector comprising the antisense construct as claimed in claim 23.

28. A cell of a potato plant whose genome comprises the antisense construct as claimed in claim 23.

29. A potato plant whose genome comprises the antisense construct as claimed in claim 23.

30. A potato tuber whose genome comprises the antisense construct as claimed in claim 23.

31. A seed from a potato plant, wherein the genome of said seed comprises the antisense construct as claimed in claim 23.

32. A microtuber of potato whose genome comprises the antisense construct as claimed in claim 23.

33. A vector comprising the antisense construct as claimed in claim 24.

34. A cell of a potato plant whose genome comprises the antisense construct as claimed in claim 24.

35. A potato plant whose genome comprises the antisense construct as claimed in claim 24.

36. A potato tuber whose genome comprises the antisense construct as claimed in claim 24.

37. A seed from a potato plant wherein the genome of said seed comprises the antisense construct as claimed in claim 24.

38. A method of suppressing amylose formation in potato, comprising:
cultivating a potato containing a gene construct comprising a fragment of a potato gene of that encodes a granule-bound starch synthase (GBSS) inserted positioned in an anti-sense orientation, wherein said fragment contains the nucleotide sequence of of SEQ ID NO. 3.

39. A method of enhancing amylopectin formation in potato, comprising:
cultivating a potato containing a gene construct comprising a fragment of a potato gene that encodes a granule-bound starch synthase (GBSS) positioned in an anti-sense orientation, wherein said fragment contains a nucleotide sequence selected from the group consisting of SEQ ID NO. 1, SEQ ID NO. 2, SEQ ID NO. 3, and nucleotide sequences that encode one or more of the amino acid sequences of SEQ.ID NOs. 6–17.

40. An isolated fragment of a potato gene that encodes a granule-bound starch synthase (GBSS), wherein said fragment contains the nucleotide sequence of SEQ ID NO. 1.

41. An antisense construct that is capable of inhibiting expression of a potato gene that encodes a granule-bound starch synthase (GBSS) comprising:

a promoter, operably linked to
a fragment of the potato gene that encodes said granule-bound starch synthase positioned in an antisense orientation, wherein said fragment contains the nucleotide sequence of SEQ ID NO. 1.

42. The antisense construct as claimed in claim 41, wherein the promoter is a granule-bound starch synthase (GBSS) gene promoter.

43. The antisense construct as claimed in claim 41, wherein the promoter is selected from the group consisting of SEQ ID NO. 4, a CaMV 35S promoter and a patatin I promoter.

44. A vector comprising a fragment of a potato gene that encodes a granule-bound starch synthase (GBSS), wherein said fragment contains the nucleotide sequence of SEQ ID NO. 1.

45. A vector comprising the antisense construct as claimed in claim 41.

46. A cell of a potato plant whose genome comprises the antisense construct as claimed in claim 41.

47. A potato plant whose genome comprises the antisense construct as claimed in claim 41.

48. A potato tuber whose genome comprises the antisense construct as claimed in claim 41.

49. A seed from a potato plant wherein the genome of said seed comprises the antisense construct as claimed in claims 41.

50. A microtuber of a potato, whose genome comprises the antisense construct as claimed in claim 41.

51. An isolated, tuber-specific potato, granule-bound starch synthase (GBSS) gene promoter that contains the nucleotide sequence of SEQ ID NO. 4.

52. An isolated tuber-specific, potato, granule-bound starch synthase (GBSS) gene promoter consisting essentially of the nucleotide sequence of SEQ ID NO. 4.

53. The method of claim 1 wherein the promoter is selected from the group consisting of a CaMV 35S promoter, a patatin I promoter, a GBSS promoter, SEQ ID NO. 4, and combinations thereof.

54. The method of claim 1 wherein suppression of amylose formation is practically complete.

55. The method of claim 1 wherein introducing is by a transformation process.

56. The method of claim 1 wherein the fragment contains SEQ ID NO. 1.

57. The method of claim 1 wherein the fragment contains SEQ ID NO. 2.

58. The method of claim 1 wherein the fragment contains SEQ ID NO. 3.

59. The method of claim 1 wherein the fragment encodes one or more of the amino acid sequences of SEQ ID NOs. 6–17.

60. The fragment of claim 2 which contains SEQ ID NO. 1.

61. The fragment of claim 2 which contains SEQ ID NO. 2.

62. The fragment of claim 2 which contains SEQ ID NO. 3.

63. The fragment of claim 2 which contains the nucleotide sequence that encodes one or more of the amino acid sequences of SEQ ID NOs. 6–17.

64. The construct of claim 3 wherein the fragment contains SEQ ID NO. 1.

65. The construct of claim 3 wherein the fragment contains SEQ ID NO. 3.

66. The construct of claim 3 wherein the fragment encodes one or more of the amino acid sequences of SEQ ID NOs. 6–17.

67. The method of claim 20 wherein the fragment contains SEQ ID NO. 1.

68. The method of claim 20 wherein suppression of amylose formation is practically complete.

69. The method of claim 21 wherein the fragment contains SEQ ID NO. 2.

70. The method of claim 21 wherein the fragment contains SEQ ID NO. 3.

71. The method of claim 21 wherein the fragment encodes the amino acid sequence of any one or more of SEQ ID NOs. 6–17.

72. The method of claim 21 wherein the gene construct further comprises a promoter.

73. The method of claim 72 wherein the promoter is selected from the group consisting of a CaMV 35S promoter, a patatin I promoter, a GBSS promoter, SEQ ID NO. 4, and combinations thereof.

74. The method of claim 21 wherein suppression of amylose formation is practically complete.

75. The method of claim 21 wherein the fragment contains SEQ ID NO. 2.

76. The method of claim 38 wherein suppression of amylose formation is practically complete.

77. The method of claim 38 wherein the gene construct further comprises a promoter.

78. The method of claim 77 wherein the promoter is selected from the group consisting of a CaMV 35S promoter, a patatin I promoter, a GBSS promoter, SEQ ID NO. 4, and combinations thereof.

79. The method of claim 39 wherein the nucleotide sequence contains SEQ ID NO. 1.

80. The method of claim 39 wherein the nucleotide sequence contains SEQ ID NO. 2.

81. The method of claim 39 wherein the nucleotide sequence contains SEQ ID NO. 3.

82. The method of claim 39 wherein the nucleotide sequence encodes one or more of the amino acid sequences of SEQ ID NOs. 6–17.

83. The method of claim 39 wherein the gene construct further comprises a promoter.

84. The method of claim 83 wherein the promoter is selected from the group consisting of a CaMV 35S promoter, a patatin I promoter, a GBSS promoter, SEQ ID NO. 4, and combinations thereof.

* * * * *